US008722045B2

(12) United States Patent
Jalkanen et al.

(10) Patent No.: US 8,722,045 B2
(45) Date of Patent: May 13, 2014

(54) CELL AND THERAPEUTICAL AND DIAGNOSTICAL METHODS BASED THEREON

(75) Inventors: Sirpa Jalkanen, Piispanristi (FI); Marko Salmi, Turku (FI); Markku Jalkanen, Piispanristi (FI)

(73) Assignee: Faron Pharmaceuticals Oy, Turku (FI)

( * ) Notice: Subject to any disclaimer, the term of this patent is extended or adjusted under 35 U.S.C. 154(b) by 64 days.

(21) Appl. No.: 13/262,088

(22) PCT Filed: Apr. 6, 2010

(86) PCT No.: PCT/FI2010/050266
§ 371 (c)(1),
(2), (4) Date: Sep. 29, 2011

(87) PCT Pub. No.: WO2010/122217
PCT Pub. Date: Oct. 28, 2010

(65) Prior Publication Data
US 2012/0027770 A1 Feb. 2, 2012

(30) Foreign Application Priority Data
Apr. 22, 2009 (FI) ..................................... 20090161

(51) Int. Cl.
*A61K 39/395* (2006.01)

(52) U.S. Cl.
USPC ..................................... 424/141.1; 424/174.1

(58) Field of Classification Search
None
See application file for complete search history.

(56) References Cited

U.S. PATENT DOCUMENTS

| 7,910,097 | B2* | 3/2011 | Jalkanen et al. | ............ | 424/130.1 |
| 2003/0211498 | A1* | 11/2003 | Morin et al. | ...................... | 435/6 |
| 2004/0191783 | A1* | 9/2004 | Leclercq et al. | ................... | 435/6 |
| 2005/0069888 | A1* | 3/2005 | Jalkanen et al. | ................... | 435/6 |
| 2008/0267958 | A1* | 10/2008 | Jalkanen et al. | ............ | 424/133.1 |

FOREIGN PATENT DOCUMENTS

| EP | 1661915 A1 | 5/2006 | | |
| WO | WO 00/55173 | * | 9/2000 | ............. C07H 21/04 |
| WO | 03057130 A2 | | 7/2003 | |

OTHER PUBLICATIONS

Byers, T., CA Journal, vol. 49, No. 6, Nov./Dec. 1999.*
Ben-Efraim, Tumor Biology 1999; 20: 1-24.*
Frazer, I., Expert. Opin. Pharmacother. 2004; 5: 2427-2434.*
Gura, Science, 1997, 278:1041-1042.*
Kaiser, Science, 2006, 313, 1370.*
Granziero et al., Eur. J. Immunol. 1999, 29:1127-1138.*
Irjala H. et al., "Mannose Receptor (MR) and Common Lymphatic Endothelial and Vascular Endothelial Receptor (CLEVER)-1 Direct the Binding of Cancer Cells to the Lymph Vessel Endothelium," Cancer Research, Aug. 2003, vol. 63, pp. 4671-4676.
Kzhyshkowska, J., "Die Rolle von Makrophagen in Entzundungen und Tumoren: neue Stabilin-1-vermittelte Prozesse," Aktuelle Dermatologie, Mar. 2008, vol. 34, No. 3, pp. 72-84.
Ammar, A. et al., "Role of CLEVER-1 in Breast Cancer Metastasis," Breast Cancer Research, May 2008, vol. 10, Suppl. 2, p. 35.
Karikoski, M. et al., "Clever-1/Stabilin-1 Regulates Lymphocyte Migration Within Lymphatics and Leukocyte Entrance to Sites of Inflammation," European Journal of Immunology, Dec. 2009, vol. 39, No. 12, pp. 3477-3487.

* cited by examiner

*Primary Examiner* — Mark Halvorson
(74) *Attorney, Agent, or Firm* — Rothwell, Figg, Ernst & Manbeck PC

(57) ABSTRACT

The invention relates to a novel cell derived from the human body, where said cell comprises a Clever-1 receptor; to a method for affecting the immune system of an individual and for treatment of diseases or conditions related to the function of the immune system and to methods for screening of cancer patients that may respond to an anti-Clever-1 therapy or for diagnosing of a pregnancy complication or for estimating the risk of such complication in a pregnant woman.

2 Claims, 10 Drawing Sheets anti-Clever-1                    anti-CD14 negat co, NS-1                   negat co, 3G6

Non transfected cells – Day 2

Control anti-Clever-1

Negative control transfected – Day 2

Clever-1 siRNA transfected – Day 2

Pooled Clever-1 siRNA transfected – Day 2

CELL AND THERAPEUTICAL AND DIAGNOSTICAL METHODS BASED THEREON

CROSS-REFERENCE TO RELATED APPLICATIONS

The present application is a national stage filing under 35 U.S.C. §371 of PCT/FI2010/050266, filed 6 Apr. 2010, which in turn claims priority to Finnish Patent Application No. 20090161, filed 22 Apr. 2009, each of which are incorporated herein by reference.

FIELD OF THE INVENTION

This invention relates to a novel cell derived from the human body, where said cell comprises a Clever-1 receptor; to a method for affecting the immune system of an individual and for treatment of diseases or conditions related to the function of the immune system and to methods for screening of cancer patients that may respond to an anti-Clever-1 therapy or for diagnosing of a pregnancy complication or for estimating the risk of such complication in a pregnant woman.

BACKGROUND OF THE INVENTION

The publications and other materials used herein to illuminate the background of the invention, and in particular, cases to provide additional details respecting the practice, are incorporated by reference.

CLEVER-1 is a protein disclosed in WO 03/057130, Common Lymphatic Endothelial and Vascular Endothelial Receptor-1. It is a binding protein that mediates adhesion of lymphocytes (and malignant tumor cells) to endothelium in both the systemic vasculature and in the lymphatics. By blocking the interaction of Clever-1 and its lymphocyte substrate it is possible to simultaneously control lymphocyte recirculation and lymphocyte migration, and related conditions such as inflammation, at the site of lymphocyte influx into, and efflux from, the tissues. WO 03/057130 also discloses that Clever-1 mediates binding of other types of leukocytes such as monocytes and granulocytes to HEV-like vessels. Thus, by blocking the interaction of Clever-1 and malignant tumor cells it became possible to control metastasis by preventing malignant cells that bind to Clever-1 from being taken up by the lymphatic vessels, and thus to prevent spread of the malignancy into the lymph nodes.

Clever-1 is expressed in lymphatic endothelial cells, certain vascular endothelial cells, but also in a subpopulation of macrophages. On macrophages Clever-1 is known to function as a scavenging receptor, which can mediate endocytic uptake of various molecules such as oxidized-LDL.

Macrophages are traditionally divided into type 1 and type 2 cells. Type 1 macrophages are classical proinflammatory macrophages, which produce large quantities of proinflammatory cytokines and co-stimulatory molecules, and are very efficient in activation of T-cell responses. Type 2 macrophages, in contrast, are immune suppressing cells, which synthesize anti-inflammatory cytokines and induce regulatory T cells and hence profoundly dampen antigen-driven T cell activation. Tumor-associated macrophages are considered harmful as they mature to type 2 macrophages within the tumor environment and suppress anti-tumor immune response (Martinez, F. O. et al. Macrophage activation and polarization. *Front. Biosci.* 13:453-461.) and mediate angiogenic switch, a crucial step in cancer growth (Lin, E. Y., and Pollard, J. W. 2007. Tumor-associated macrophages press the angiogenic switch in breast cancer. *Cancer Res.* 67:5064-5066).

Pregnancy poses a challenge to the immune system, since half of the fetal antigens comes from the paternal origin, which is foreign to the mother. Several immune suppressing mechanisms are known to operate in the placenta to prevent the rejection of the fetus, which can be regarded as a semiallograft for the maternal immune system. Among the best known examples are expression of non-classical MHC molecules, inhibition of the NK-cell activity, induction of T regulatory cell activity, induction T cell apoptosis and inhibition of complement activation. The suppression of antigen presenting cell activity can also contribute to the induction of tolerance. Among the antigen presenting cells macrophages are prominently present in the placenta.

SUMMARY OF THE INVENTION

We have now identified a new subtype of macrophages in tumors, in the placenta, and also in the blood of pregnant women. This new cell can be defined as a a type 2 macrophage cell that also expresses a Clever-1 receptor. We have designated this cell as a "type 3 macrophage". This new "type 3 macrophage" is, like type 2 macrophages, an immune suppressing cell. By modulating (counteracting or stimulating, respectively) the Clever-1 receptor on this new cell, we have surprisingly found that this is a method for affecting the immune system in an individual. Counteracting or downregulation of the receptor reduces the size of malignant tumor and/or malignant tumor growth. Stimulating or upregulating of the receptor is useful in generation of fetomaternal tolerance and for prevention of pregnancy complications.

Thus, according to one aspect, this invention concerns an isolated cell (type 3 macrophage) which is a type 2 macrophage cell that comprises a Clever-1 receptor, wherein said cell is derived from an individual's tumor or placenta, or from the blood of a pregnant woman.

According to another aspect, the invention concerns a method for affecting the immune system of an individual and for treatment of diseases or conditions related to the function of the immune system, said method comprising modulating the Clever-1 receptor on the novel cell (i.e. the "type 3 macrophage") in said individual.

According to a third aspect, the invention concerns a method for screening of cancer patients that may respond to an anti-Clever-1 therapy, said method comprising
a) detecting or quantifying of the level of Clever-1 protein in a tumor sample derived from said patient,
b) comparing the result to a control, and
c) attributing an increased level of Clever-1 protein in the sample to a responsiveness to said therapy.

According to a fourth aspect, the invention concerns a method for diagnosing of a pregnancy complication or for estimating the risk of such complication in a pregnant woman, said method comprising
a) detecting or quantifying the level of Clever-1 protein in a tissue or body fluid from said woman,
b) comparing the result to a control, and
c) attributing a lack of or a decreased level of Clever-1 protein to a pregnancy complication or a risk therefore.

DETAILED DESCRIPTION OF THE INVENTION

Definitions and Preferred Embodiments

Figure 1A:
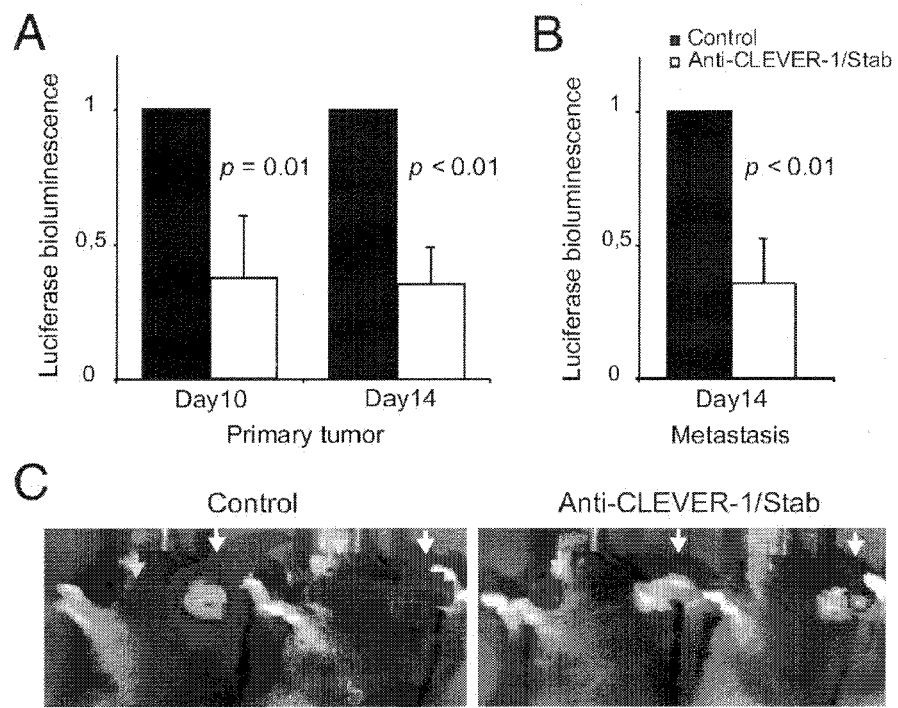
FIG. 1A. Anti-Clever-1 treatment is effective in melanoma. B16-luc melanoma cells were injected subcutaneously into the ear. Growth of the primary tumor and development of metastases were followed by IVIS chemiluminescence detection system. (A) Relative size (mean±SEM) of the primary tumor after 10 and 14 days in the two treatment groups. (B) Relative size (mean±SEM) of metastases at the end of the experiment (day 14). The size of the primary tumor and metastases in the control treated group is 1.0 by definition. (C) Examples of animals treated with anti-Clever-1 or control antibody. In the left panel, the second and fourth arrows point to the injection site (primary tumor) and first and third arrows point to the neck metastases. In the right panel, the second and third arrows point to the injection site (primary tumor) and the first arrow points to the neck metastases. Note that one anti-Clever-1 antibody treated mouse does not have a detectable tumor at the site of injection and the other one does not have neck metastases. N=12 in both groups.

The term "CLEVER-1" is used to denote the protein disclosed in WO 03/057130, Common Lymphatic Endothelial and Vascular Endothelial Receptor-1, a binding protein that mediates adhesion of lymphocytes (and malignant tumor cells) to endothelium in both the systemic vasculature and in the lymphatics. The nucleotide sequence (7879 nt) and amino acid sequence of Clever-1 is shown in SEQ ID NO. 1. In the nucleotide sequence of Clever-1 there are four nucleotide differences compared to Genebank entry AJ 2752213 (stabilin-1), i.e., nucleotides 1131, 2767, 6629 and 6969.

The term "type 2 macrophage" shall be understood as an immune suppressing macrophage which expresses a mannose receptor.

The term "type 3 macrophage" shall be understood as a subpopulation of type 2 macrophages that in addition to the mannose receptor also expresses the Clever-1 receptor. The Clever-1 receptor on the type 3 macrophage cell can be either the entire sequence (SEQ ID NO. 1), a slight modification thereof (such as Stabilin-1) or a fragment thereof.

The term "treatment" or "treating" shall be understood to include complete curing of a disease or disorder, as well as amelioration or alleviation of said disease or disorder.

The term "prevention" shall be understood to include complete prevention, prophylaxis, as well as lowering the individual's risk of falling ill with said disease or disorder.

The term "individual" refers to a human or animal subject.

The term "effective amount" is meant to include any amount of an agent according to the present invention that is sufficient to bring about a desired therapeutic result, especially upon administration to an animal or human subject.

The term "inhibiting" or "inhibition" shall be understood to include not only complete inhibition but also any grade of suppression.

In one embodiment, the method for affecting the immune system of an individual by modulating of the Clever-1 receptor on the type 3 macrophage cell can be used for reducing the size of malignant tumor and/or by reducing malignant tumor growth in an individual. In this embodiment, an effective amount of an agent capable of counteracting the influence of or for down-regulating the expression of the Clever-1 protein is administered to the individual.

In another embodiment, the method for affecting the immune system of an individual by modulating of the Clever-1 receptor on the type 3 macrophage cell can be used for maintaining feto-maternal tolerance and/or prevention of a pregnancy complication in a pregnant woman. In this embodiment, to the pregnant woman is administered either
i) an effective amount of an agent, which up regulates the expression of the Clever-1 protein or which stimulates said protein, or
ii) in vitro cultivated type 3 macrophage cells.
Preferred Agents The term "an agent capable of counteracting the influence of Clever-1" shall be understood to include peptides or proteins (such as soluble Clever-1 or Clever-1 antagonist antibodies) blocking the Clever-1 protein as well as any inhibitors, particularly small molecule inhibitors, useful to inhibit the protein activity. Particularly useful agents are antibodies.

The term "an agent capable of down-regulating the expression of Clever-1" shall be understood to include antisense oligonucleotides, small interfering RNAs (siRNA) as well as ribozymes, or vectors being capable of expressing them, or essential parts thereof, in vivo.

The term "antibody" is used in the broadest sense and specifically covers single monoclonal antibodies (including agonist and antagonist antibodies), polyclonal antibodies, as well as antibody fragments and single chain antibodies (e.g., Fab, F(ab')$_2$, Fv), so long as they exhibit the desired biological activity. Papain digestion of antibodies produces two identical antigen binding fragments, called Fab fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen. Single chain "Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. See, Ladner et al., U.S. Pat. No. 4,946,778, and Bird, R. E. et al., *Science*, 242:423-426 (1988).

The term "antibody" shall be understood to include also chimeric, humanized or primatized (CDR-grafted) antibodies, as well as chimeric or CDR-grafted single chain antibodies, and the like, comprising portions derived from different species. "Chimeric" antibodies (immunoglobulins) have a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., U.S. Pat. No. 4,816,567; Morrison et al., *Proc. Natl. Acad. Sci. USA* 81:6851-6855 (1984). The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567. See also, Newman, R. et al., BioTechnology 10: 1455-1460 (1992), regarding primatized antibody.

Particularly preferred Clever-1 antagonist antibodies are the monoclonal antibodies 3-266 (DSM ACC2519) and 3-372 (DSM ACC2590), both deposited under the terms of the Budapest Treaty on the International Recognition of the Deposit of Micro-organisms for the Purposes of Patent Procedure on Aug. 21, 2001, with DSMZ-Deutsche Sammlung von Mikroorganismen and Zellkulturen GmbH, Mascheroder Weg 1b, D-38124 Braunschweig. See WO 03/057130.

For treatment of human individuals, humanized or chimeric or primatized variants of the monoclonal antibodies mentioned above are preferred.

Preferable inhibitors are small molecule inhibitors.

Preferably, the agent capable of down-regulating the expression of Clever-1, is a small interfering RNAs (siRNA) or an expression vector comprising nucleic acid encoding the siRNA duplex or the antisense strand of the duplex in a manner which allows expression of the siRNA duplex or antisense strand within a mammalian cell. Such siRNA duplexes for another protein, VAP-1, are described in WO 2006/134203.

The principle of siRNA is extensively presented in literature. As examples can be mentioned the US patent publications 2003/0143732, 2003/0148507, 2003/0175950, 2003/0190635, 2004/0019001, 2005/0008617 and 2005/0043266. An siRNA duplex molecule comprises an antisense region and a sense strand wherein said antisense strand comprises sequence complementary to a target region in an mRNA sequence encoding a certain protein, and the sense strand comprises sequence complementary to the said antisense strand. Thus, the siRNA duplex molecule is assembled from two nucleic acid fragments wherein one fragment comprises the antisense strand and the second fragment comprises the sense strand of said siRNA molecule. The sense strand and antisense strand can be covalently connected via a linker molecule, which can be a polynucleotide linker or a non-nucleotide linker. The length of the antisense and sense strands are typically about 19 to 21 nucleotides each. Typically, the antisense strand and the sense strand both comprise a 3'-terminal overhang of a few, typically 2 nucleotides. The 5'-terminal of the antisense is typically a phosphate group (P). The siRNA duplexes having terminal phosphate groups (P) are easier to administrate into the cell than a single stranded antisense. In the cell, an active siRNA antisense strand is formed and it recognizes a target region of the target mRNA. This in turn leads to cleaving of the target RNA by the RISC endonuclease complex (RISC=RNA-induced silencing complex) and also in the synthesis of additional RNA by RNA dependent RNA polymerase (RdRP), which can activate DICER and result in additional siRNA duplex molecules, thereby amplifying the response.

The term "complementary" means that the nucleotide sequence can form hydrogen bonds with the target RNA sequence by Watson-Crick or other base-pair interactions. The term shall be understood to cover also sequences which are not 100% complementary. It is believed that also lower complementarity might work. However, 100% complementarity is preferred.

The siRNA shall, when used as a pharmaceutical, be introduced in a target cell. The delivery can be accomplished in two principally different ways: 1) exogenous delivery of the oligonucleotide or 2) endogenous transcription of a DNA sequence encoding the oligonucleotide, where the DNA sequence is located in a vector.

Normal, unmodified RNA has low stability under physiological conditions because of its degradation by ribonuclease enzymes present in the living cell. If the oligonucleotide shall be administered exogenously, it is highly desirable to modify the molecule according to known methods so as to enhance its stability against chemical and enzymatic degradation.

Modifications of nucleotides to be administered exogenously in vivo are extensively described in the art. Principally, any part of the nucleotide, i.e the ribose sugar, the base and/or internucleotidic phosphodiester strands can be modified.

It should be stressed that the modifications mentioned above are only non-limiting examples.

A useful target region can easily be identified by using any of the numerous academic or commercially affiliated algorithms that have been developed to assist scientists to locate utilizable siRNA sequences. As examples of such software systems can be mentioned siDirect http colon//design dot RNAi dot jp Nucleic Acids Res. 2004 Jul. 1; 32: W124-9); TROD (T7 RNAi Oligo Designer (http colon//www dot cellbio dot unige dot ch/RNAi dot html; Nucleic Acids Res. 2004 Jul. 1; 32: W121-3); DEQOR http colon//cluster-1 dot mpi-cbg dot de/Deqor/deqor dot html; Nucleic Acids Res. 2004 Jul. 1; 32: W113-20) or programs available at http colon// www dot genscript dot com; http colon//www dot genscript dot com/rnai dot html#design or http colon www dot genscript dot com/sirna_ca dot html#design; Bioinformatics 2004 Jul. 22; 20 (11)1818-20. An essential criterion of the tools is to achieve siRNA:s with maximum target-specificity for mammalian RNA interference where off-target gene silencing is avoided. The usefulness of any sequence identified by such algorithms should thereafter be verified by experiments.

Preferred agents for stimulating the Clever-1 protein are, for example agonist antibodies and small molecule agonists. By "agonist antibody" is meant an antibody which is able to bind to Clever-1 and facilitate adhesion of other tissue.

Preferred small molecule agonists are immune suppressing agents, such as an anti-inflammatory agents, especially interleukins such as, interleukin-4, interleukin-13 or steroid hormones such as dexamethasone, or a combination thereof.

For maintaining feto-maternal tolerance and/or prevention of a pregnancy complication in a pregnant woman, also administration of the type 3 macrophages having been cultivated in vitro, is possible.

Diseases Responding to the Treatment

The method for treating or preventing cancer by reducing the size of malignant tumor and/or by reducing malignant tumor growth according to this invention is applicable to all forms of cancers. Thus, any benign or malignant tumor or metastasis of malignant tumor, such as skin cancer and colon cancer can be treated. Also leukemias, lymphomas and multiple myelomas can be treated. Particularly, melanomas and lymphomas respond very well to the treatment.

We believe that the method according to this invention is useful in the treatment or prevention of all kinds of sarcomas, for example fibrosarcoma, liposarcoma, chondrosarcoma, osteosarcoma, angiosarcoma, lymphangiosarcoma, leiomyosarcoma, and rhabdomyosarcoma, mesothelioma, meningioma, leukemias, lymphomas, as well as all kinds of carcinomas, such as squamous cell carcinomas, basal cell carcinoma, adenocarcinomas, papillary carcinomas, cystadenocarcinomas, bronchogenic carcinomas, melanomas, renal cell carcinomas, hepatocellular carcinoma, transitional cell carcinomas, choriocarcinomas, seminomas, and embryonal carcinomas.

By stimulating of Clever-1, it is possible to main feto-maternal tolerance and/or prevent pregnancy complications in a pregnant woman. Pregnancy complications that can be treated are especially risk of spontaneous abortion and pre-eclampsia.

Administration Routes, Formulations and Required Dose

The pharmaceutical compositions to be used in the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, ocular routes or via inhalation. Alternatively, administration can be by the oral route. Particularly preferred for small molecule inhibitors may be oral administration. In addition to the pharmacologically active compounds, the pharmaceutical preparations of the compounds preferably contain suitable pharmaceutically acceptable carriers comprising excipients and auxiliaries that facilitate processing of the active compounds into preparations that can be used pharmaceutically.

For reducing the size of malignant tumor and/or by reducing malignant tumor growth, intra-tumoral administration may be useful.

For maintaining feto-maternal tolerance and/or prevention of a pregnancy complication in a pregnant woman, intra-placental administration of the effective agent may also be useful.

The siRNA duplex for use in this invention can be administered to the individual by various methods. According to one method, the siRNA may be administered exogenously as such, or in the form of a pharmaceutical composition admixed with a suitable carrier which may be, for example, a liposome, cholesterol, lithocholic acid, lauric acid, a cationic lipid, polyethylenimine (PEI) or its conjugates with polyethylene glycol (PEG) derivatives. However, also other carriers can be used. The siRNA can be administered systemically or locally. As suitable routes of administration can be mentioned intravenous, intramuscular, subcutaneous injection, inhalation, oral, topical, ocular, sublingual, nasal, rectal, intraperitoneal delivery and transdermal delivery systems. The composition containing the siRNA can, instead of using direct injection, also be administered by use of, for example, a catheter, infusion pump or stent.

Another method to achieve high concentrations of the siRNA in cells is to incorporate the siRNA-encoding sequence into an expression vector and to administer such a vector to the individual. In this application, the expression vector could be construed so that either the siRNA duplex or only the antisense strand thereof is expressed, e.g. in the form of short hairpin RNAs. The expression vector can be a DNA sequence, such as a DNA plasmid capable of eukaryotic expression, or a viral vector. Such a viral vector is preferably based on an adenovirus, an alphavirus, an adeno-associated virus or a retrovirus. Preferably, the vector is delivered to the patient in similar manner as the siRNA described above. The delivery of the expression vector can be systemic, such as intravenous, intramuscular or intraperitoneal administration, or local delivery to target tissue or to cells explanted from the patient, followed by reintroduction into the patient. Since intravenous administration of siRNA preferentially targets liver vasculature (Lewis D L and Wolff J A, Methods Enzymol. 2005; 392:336-50; Soutschek J et al., Nature. 2004 Nov. 11; 432 (7014):173-8; and Song E et al., Nat. Med. 2003 March; 9 (3):347-51), diseases of liver are especially suitable targets for intervention. Especially siRNA:s embedded in liposomes have been reported to be very useful for targeting liver tissue. No toxic side-effects have been reported.

Thus, a typical dose is in the dosage range of about 0.1 microgram/kg to about 300 mg/kg, preferably between 1.0 microgram/kg to 10 mg/kg body weight. Compounds for use in the present invention may be administered in a single daily dose, or the total daily dosage may be administered in divided doses of two, three or four times daily. When siRNA is used, a typical daily dose is in the dosage range of about 1 mg/kg to about 20 mg/kg, preferably about 5 mg/kg body weight. The suitable administration frequency is believed to be 1 to 2 doses daily. When the RNAi is delivered by an expression vector, a single dose (or a single doses repeated at certain intervals, e.g. once in week) is believed to be enough.

Diagnostic Methods:

The method for detection or quantification of Clever-1 may be based on detecting or quantifying the level of the Clever-1 protein in a tissue or body fluid by
i) determining the Clever-1 mRNA expression from said tissue or body fluid by RT-PCR, or by a hybridizing technique, or
ii) subjecting the tissue or body fluid expected to contain the Clever-1 protein to an binder (such as antibody, affibody or aptamer) recognizing said Clever-1, and detecting and/or quantifying said binder, or subjecting said tissue or body fluid to analysis by proteomics technique.

The hybridizing technique include, for example DNA hybridization and northern blot. The detection or quantification of the antibody or other binder can be performed according to standard immunoassay protocols, such as label-linked immunosorbent assays, western blot and immunohistochemical methods The invention will be illuminated by the following non-restrictive Experimental Section.

EXPERIMENTAL SECTION

Materials and Methods

Animals. Balb/C and C57B16 mice (6-9 weeks old) and New Zealand white (NZW) rabbits were used in the in vivo experiments. The Local Ethical Committee approved the experimental procedures that were used in this study.

Tumor cell lines. KCA, a human lymphoblastoid cell line was a kind gift from E. Engleman (Stanford University, CA). B16-F10-luc-G5 melanoma cell line containing a luciferase construct was purchased from Xenogen (Alameda, Calif.). Tumor cells were cultured in RPMI 1640 (KCA) and MEM/HBSS (B16 melanoma) (HyClone, Logan, Utah) supplemented with 10% FBS (Invitrogen, Gibco), non-essential amino acids (Biologial Industries, Haemek, Israel), 200 mM L-glutamine (B10 Whittaker, Walkersville, Md.), 1 mM Sodium pyruvate (Invitrogen, Gibco), and MEM Vitamin solution (Invitrogen, Gibco, Paisley, UK).

Tumor cell migration via lymphatics in rabbits. Rabbits were given 3-372 (anti-Clever-1, n=8) or control antibody (n=9) 2 mg/kg i.v. one day before and on the same day as the lymphoma cell transfer. In addition 0.5 mg of antibodies were added to the CFSE-labeled KCA lymphoma cell suspension that was given subcutaneously into the footpads. After 24 hours from the cell transfer, popliteal lymph nodes were collected and cell suspensions were analysed by flow cytometry.

Lymphatic metastasis model. B16-F10-luc-G5 melanoma cells at a dose of 400,000 cells in 30 µl of RPMI 1640 (GIBCO) were injected subcutaneously into the left ear of mice. Inoculated tumors can be seen as black nodules through the skin. Tumor growth was measured by luciferase bioluminescence (Marttila-Ichihara, F. et al. Blood 112:64-72) twice a week. In brief, mice were anesthetized with 2.5% isoflurane (Becton Dickinson). One hundred fifty mg/kg of substrate D-luciferin sodium salt (Synchem, Kassel, Germany) was injected intraperitoneously to mice 10 min before imaging. A black and white photographic image was taken in the black chamber with a cooled (−70 C) CCD camera (IVIS; Xenogen, Alameda, Calif.). Signal intensity was quantified as the photon counts using the Living Image software (Xenogen). One day before tumor injection, twelve C57B1/6J mice were treated with anti-Clever-1 (Schledzewski, K. et al. *J. Pathol.* 209:67-77) antibody and the same number of mice were treated with NS-1 control antibody with subcutaneous injection of the antibodies at a dose of 50 µg into the ear. Intraperitoneal antibody administration at a dose of 100 µg was started one day after tumor injection and then repeated every third day. Mice were sacrificed on day 14.

Immunohistochemistry. Acetone fixed frozen sections of the ear and peripheral lymph node metastases of the mice were stained with rat mAb against macrophage mannose receptor (MR, MR5D3, a marker for type 2 macrophages, kind gift from L. Martinez-Pomares), PV-1 antigen (blood vessel antigen, MECA-32, kind gift from E. Butcher, Stanford University, CA), CD31 (a marker of both blood and lymphatic vessels; BD Pharmingen), CD3 (BD Pharmingen), CD8 (Caltag) or with a negative control mAb (Hermes-1 against human CD44). FITC-conjugated anti-rat Ig (Sigma) diluted in PBS containing 5% normal mouse serum was used as the second stage antibody. Tumor tissues, metastases and lymph node sections were also stained using biotinylated anti-Clever-1 followed by Streptavidin-Alexa Fluor 546. For Foxp3 expression, frozen sections were fixed with 2% paraformaldehyde, stained with anti-Foxp3 (eBioscience) followed by peroxidase-conjugated rabbit anti-rat Ig (Dako, Denmark). 3,3'-diaminobenzidine hydrochloride in PBS containing 0.03% hydrogen peroxide was used as a chromogen and the sections were counterstained with hematoxylin. The sections were analyzed using Olympus BX60 microscope and cell^D version 2.6 software (Soft Imaging Solutions GmbH). SPARC stainings were analyzed using Image J software.

Immunizations. Rabbits were immunized to the footpads with a cocktail (volume 200 ml) containing heat killed *Salmonella enteritidis*, *E. coli* LPS (10 mg) and bovine serum albumin (1 mg). At the same time the rabbits received either anti-Clever-1 antibody (3-372, n=5) or class matched negative control antibody (NS-1, n=5) 2 mg/kg. Non-immunized rabbits were used as controls. The antibody treatments were repeated on day 2, 4, 7 and 9. Immunization was repeated on day 7. Serum samples were collected on day 7 and 11 and antibody titers were analyzed by ELISA. Briefly, polystyrene microtiter plates (Nunc, Roskilde, Denmark) were coated with pretested concentrations of *E. coli* LPS (Difco Laboratories, Detroit, USA), SDS-extract of *Salmonella enteritidis* and BSA (fraction V, ICN Biomedicals, Inc. Ohio, USA). After incubation with serum samples IgM and IgG antibodies in the wells were detected with alkaline-phosphatase-conjugated anti-rabbit IgM (Southern Biotechnology Associates, Birmingham, Ala., USA) and anti-rabbit IgG (Dako Patts A/S, Copenhagen, Denmark). The absorbances were detected with a Victor multilabel counter (Wallac, Turku, Finland) at a wavelength of 405 nm.

Mice were immunized with subcutaneous injection of 50 µg ovalbumin (OVA, grade V; Sigma, St Louis, Mo.) in incomplete Freund's adjuvant into the footpads. Immunizations were repeated three times (on day 0, 7 and 14). Mice were treated one hour before first immunization with subcutaneous injection of anti-Clever-1 or control antibody (NS-1), 50 µg/mouse, n=6+6) and intraperitoneally three times a week (100 µg/mouse). Mice were sacrificed on day 17 and popliteal lymph nodes, inguinal lymph nodes and spleens were collected and cells were isolated for flow cytometric analyses and for proliferation assay. Spleens were homogenized and red cells were lysed using hypotonic saline. T cells ($0.2 \times 10^6$) were co-cultured with increasing concentration (0-2 mg/ml) of OVA in round-bottom 96-well plates. Co-cultures were incubated in HEC-medium for 3 d and pulsed with $^3$H-thymidine (1 µCi [0.037 MBq] per well) for the final 6 h. Cells were harvested using semi-automated plate harvester (Tomtech MACH III; Fisher Scientific, Hampton, N.H.) and counted with the 1450 Microbeta counter (Wallac). The antibody titers against OVA were determined by ELISA as described (Stolen, C. M. et al., *Immunity* 22:105-115). The phenotype analyses were carried out as explained above. In addition, FoxP3 positive regulatory T cells were detected using a kit from eBioscience according to the manufacturer's instructions.

Results

Antitumor Effect:

Under Clever-1 Treatment Both Primary Tumor and Metastases of Melanoma Remain Small.

Figure 1B:
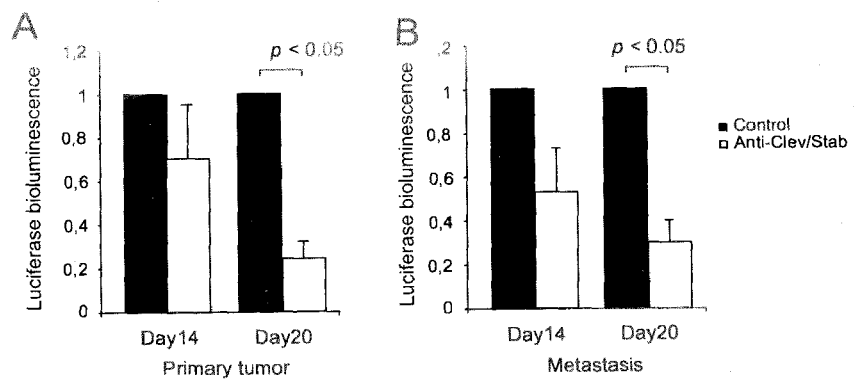
FIG. 1B. The figure shows the development of primary tumor (A) and metastases (B) when the antibody treatment was started three days after the injection of B16 melanoma cells (day 14, n=12 in both groups and day 20, n=6 in both groups).

To study, whether targeting Clever-1 can have beneficial effects on tumor development we utilized B16 melanoma model in mouse. Both the primary tumors in the ear and the metastases in the draining lymph nodes in the neck reached only about 30% of the size when treated with anti-Clever-1 antibody in comparison to the control treated animals (FIG. 1A, A-C). Because in clinical settings the treatments are started after the malignant growth has been diagnosed, we also made sets of experiments better mimicking the clinical situation. In these experiments, we let the tumors grow three days before starting the antibody therapy and completed the experiment either on day 14 or 20 after the tumor cell injections. Also in these experimental set ups the antibody therapy was effective leading to statistically significant reduction in primary tumors and metastases on day 20 (FIG. 1B, A and B).

Anti-Clever-1 Treatment Reduces Number of Type 2 Macrophages and Regulatory T Cells but is not Anti-Angiogenic.

Figure 2:
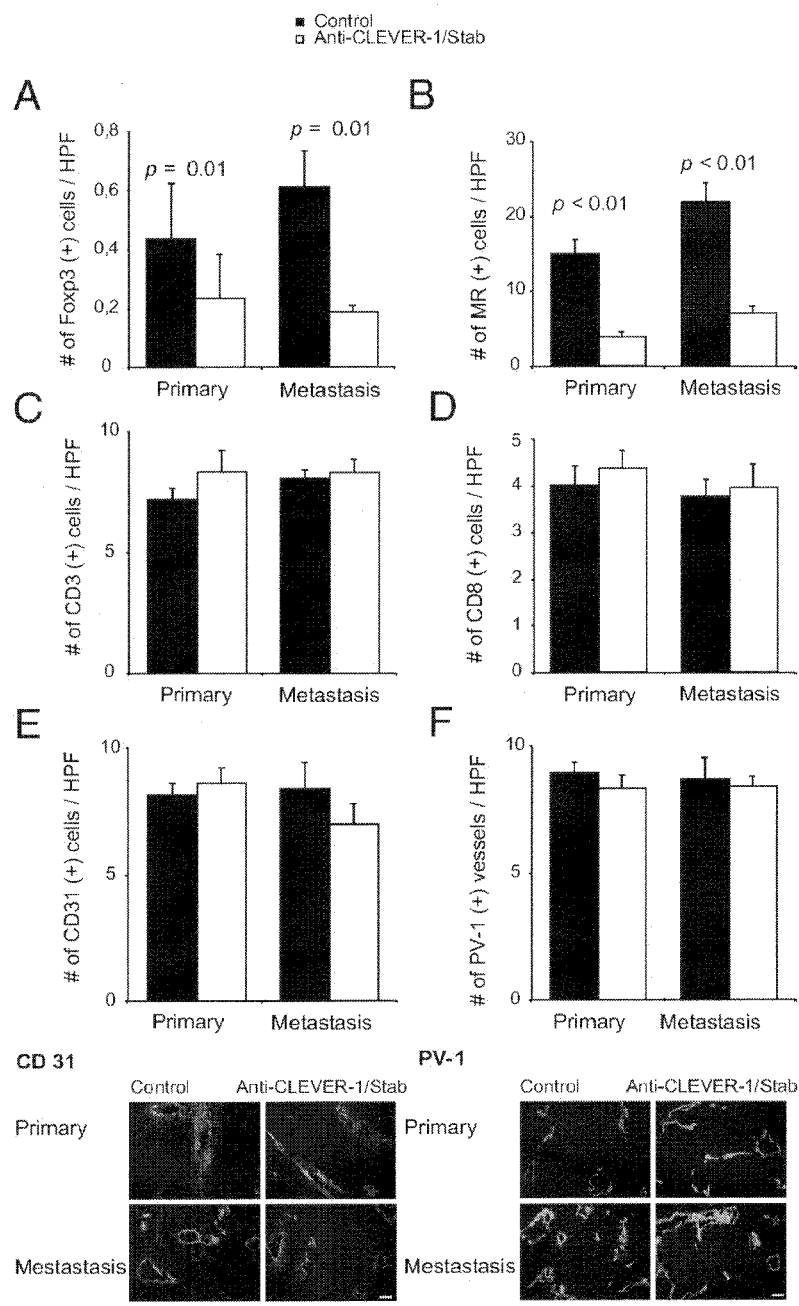
FIG. 2. Anti-Clever-1 treatment reduces number of type 2 macrophages and regulatory T cells in tumors but does not affect the vasculature. (A) Number of regulatory T cells. (B) Number of type 2 macrophages. (C) Number of CD3 positive T cells. (D) Number of CD8 positive T cells. (E) Number of CD31 positive vessels and examples of immunofluorescence staining of primary tumors and metastases with anti-CD31 antibody of anti-Clever-1 treated and control antibody treated mice. (F) Number of PV-1 positive vessels detected with anti-MECA-32 antibody and examples of immunofluorescence staining of primary tumors and metastases with anti-MECA-32 antibody of anti-Clever-1 treated and control antibody treated mice. HPF (high power field). Bar 100 µm.

Inhibition of melanoma cell migration via afferent lymphatics into the draining lymph nodes could explain the reduced size of the metastases subsequent to antibody therapy. However, it cannot give explanation for the small size of the primary tumors. Therefore we analyzed the number of different subpopulations of tumor infiltrating leukocytes and vessels. The number of tumor infiltrating leukocytes could reflect the efficacy of anti-tumor immune response and the number of vessels the angiogenic activity that controls tumor growth (Dirkx, A. E. e al. *J. Leukoc. Biol.* 80:1183-1196). The latter aspect is also relevant regarding Clever-1 itself, because it has been reported to contribute to angiogenesis in vitro (Adachi, H., and Tsujimoto, M. 2002. *J. Biol. Chem.* 277: 34264-34270). The number of type 2 macrophages and regulatory T cells was greatly diminished both in primary tumors and metastases (FIGS. 2A and 2B). This reduction was selective as the number of CD3 and CD8 positive cells were comparable in both treatment groups (FIGS. 2C and 2D). The number of blood and lymphatic vessels (CD31 and/or PV-1 positive) and their density was the same after anti-Clever-1 and control antibody therapy (FIGS. 2E and 2F). Thus, the number of the regulatory immune cell types is diminished subsequent to targeting Clever-1 but both the blood and lymphatic vasculature seem to remain intact.

Type 2 Macrophages in Melanoma are Clever-1 Positive and Antibody Therapy does not Completely Eliminate them.

A possible explanation for the diminished number of type 2 macrophages subsequent to anti-Clever-1 treatment is that the treatment kills the Clever-1 positive macrophages by complement mediated killing. However, this is not the case as 50.3±16.9% of type 2 macrophages in anti-Clever-1 and 65.9±16.7% of control antibody treated tumors are Clever-1 positive in primary tumors (FIG. 3A), although their absolutely numbers are greatly diminished due to the antibody treatment (FIG. 2B). In this context, however, it should be noted that Clever-1 positive macrophages were smaller and dimmer after anti-Clever-1 treatment than after control treatment.

Antibody Therapy does not Significantly Impair Normal Immune Response.

Figure 3:
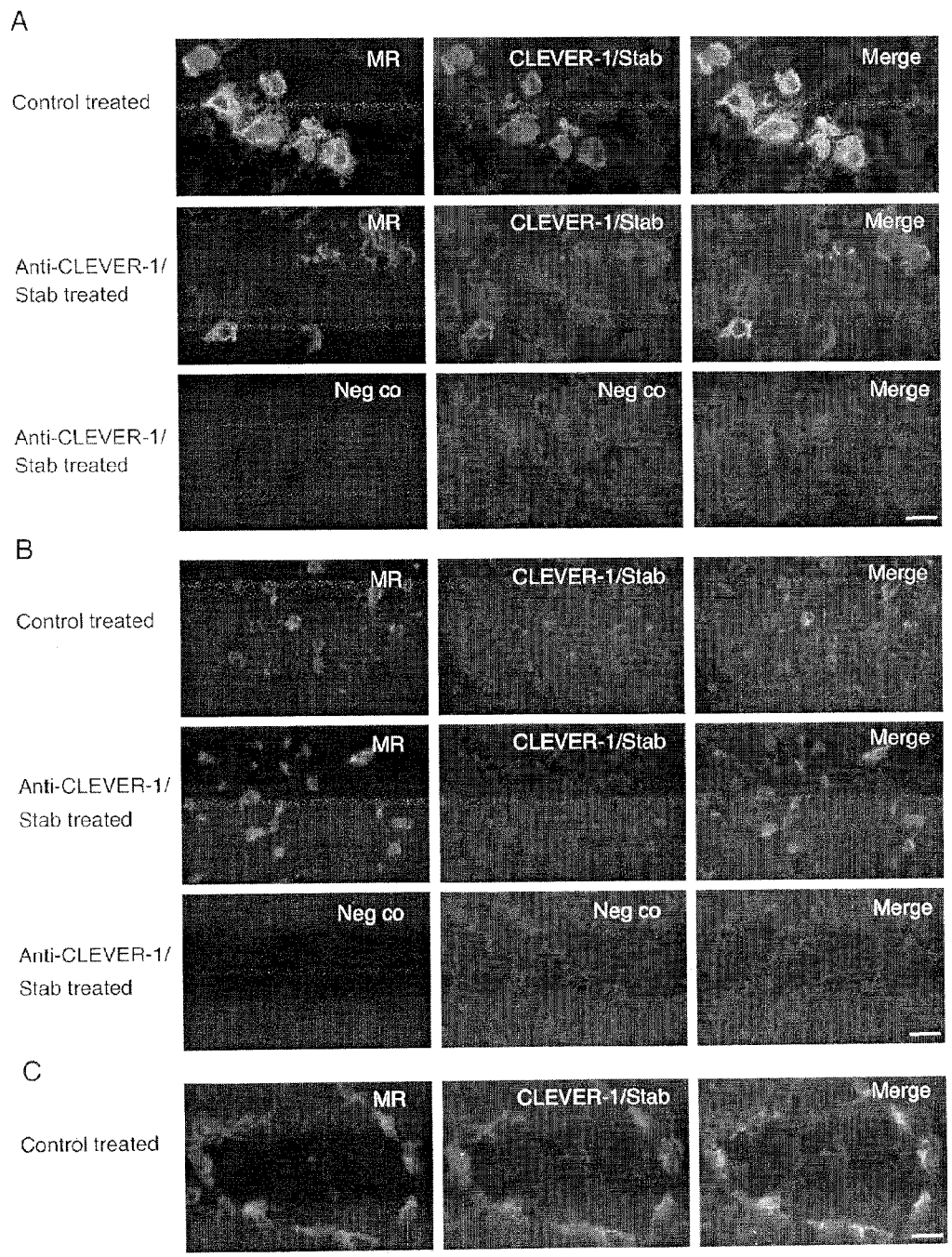
FIG. 3. Tumor associated type 2 macrophages express Clever-1 but they are absent in lymph nodes subsequent to immunization. (A) Immunofluorescence staining of melanoma metastases of anti-Clever-1 and control treated mice. Double staining with anti-MR shown in left panels and anti-Clever-1 shown in center panels. (B) Immunohistochemical stainings of macrophages in popliteal lymph nodes after immunization with OVA. MR shown in left panels, Clever-1 shown in center panels. (C) Staining of lymphatic endothelium of the same popliteal lymph nodes after OVA immunization. MR shown in left panels, Clever 1 shown in center panels. Bars, (A) and (B) 50 µm, (C) 100 µm.
Figure 4:
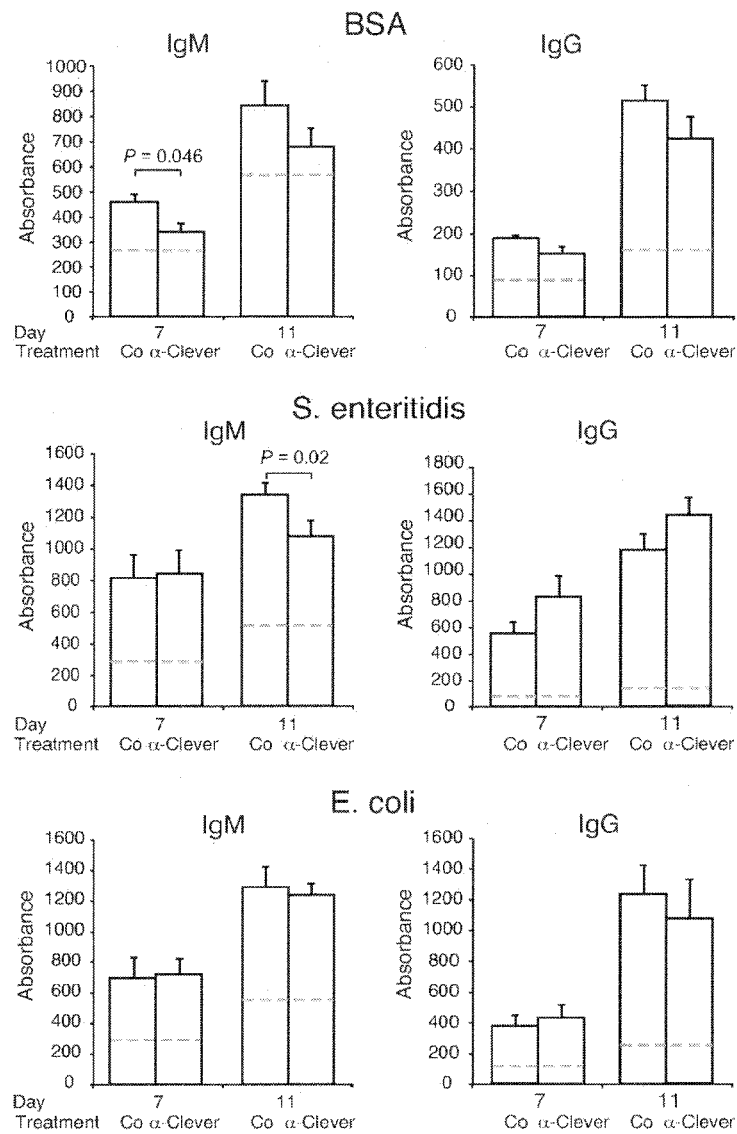
FIG. 4. Anti-Clever-1 treatment does not significantly impair the antibody response. Rabbits were immunized with BSA, heat killed *Salmonella enteritidis* and *E. coli* LPS and treated either with anti-Clever-1 or control antibody. The antibody titers were measured on days 7 and 11 after primary immunization using ELISA. The dashed line indicates the titers in non-immunized animals (receiving the antibody).
Figure 5:
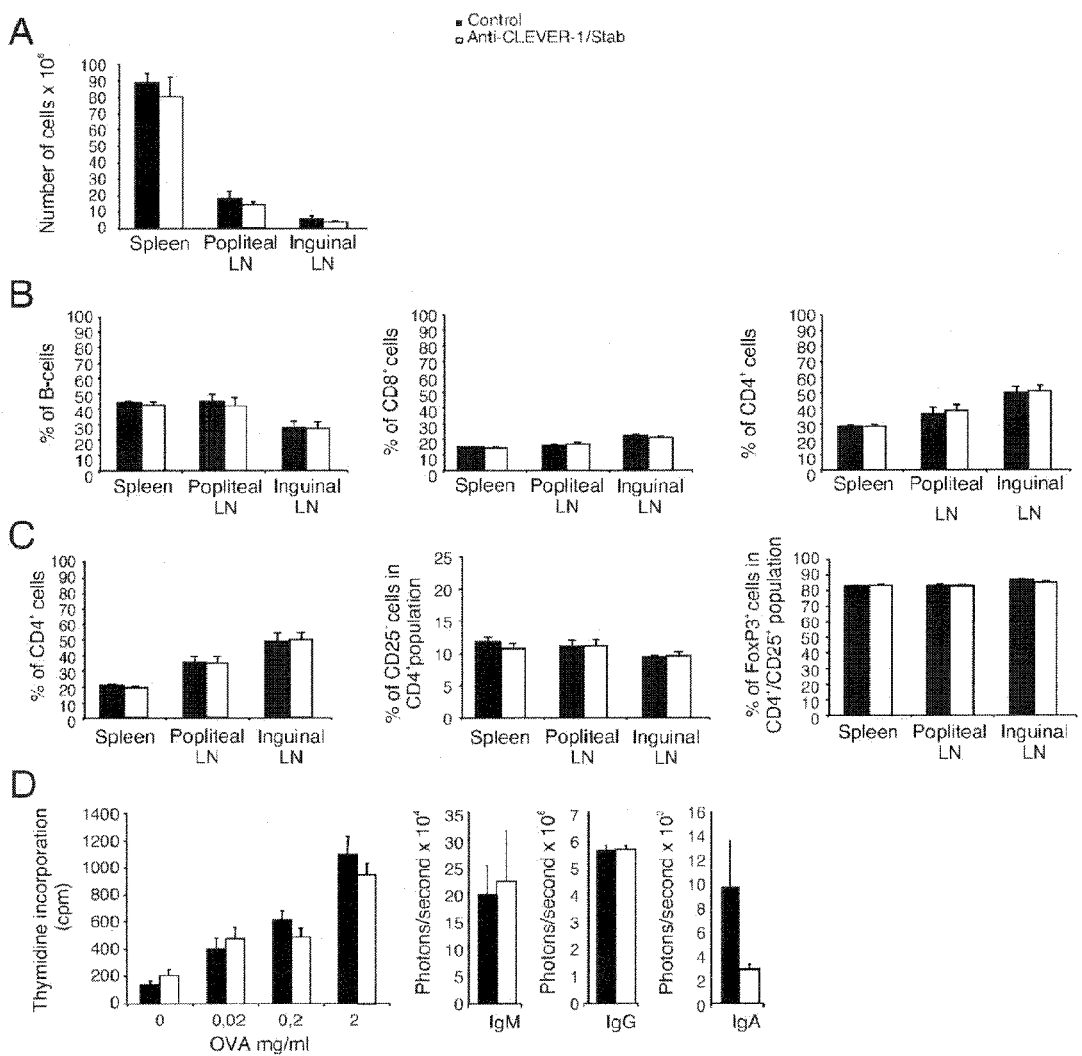
FIG. 5. Anti-Clever-1 treated mice respond normally to OVA immunization. (A) Number of lymphocytes in the indicated organs. (B) Percentages of B cells, CD4 and CD8 positive T cells. (C) Percentages of regulatory T cells. (D) Proliferation responses and antibody titers to OVA.

Since the Clever-1 blockade significantly prevents lymphocyte and tumor cell migration into the draining lymph nodes, it may also affect the normal immune response. We tested this possibility both in the rabbit and mouse models. Rabbits were treated either with anti-Clever-1 or a control antibody and immunized into the footpad with BSA, *Salmonella enteritidis* and *E. coli* LPS (FIG. 4). No statistically significant differences were detected in antibody responses of IgM and IgG classes. The only exceptions were slight decreases in the IgM response at day 7 in BSA and day 11 in *Salmonella enteritidis* in the rabbits treated with anti-Clever-1 antibody. Mice were immunized into the footpads with OVA. Absolute lymphocyte numbers and percentages of different subpopulations in lymph nodes and spleen of both treatment groups were comparable (FIGS. 5A-C) as well as the OVA-specific T and B cell responses (FIG. 5D). In contrast to MR positive type 2 macrophages within the melanoma, the MR positive macrophages were Clever-1 negative in popliteal lymph nodes of the normal and immunized mice while the lymphatic endothelium was Clever-1 positive (FIGS. 3B and 3C). Also the MR positive macrophages within the lymph nodes were markedly smaller than in the tumors suggesting that MR+/Clever-1+ macrophages within the tumor is a unique subtype.

Figure 10:
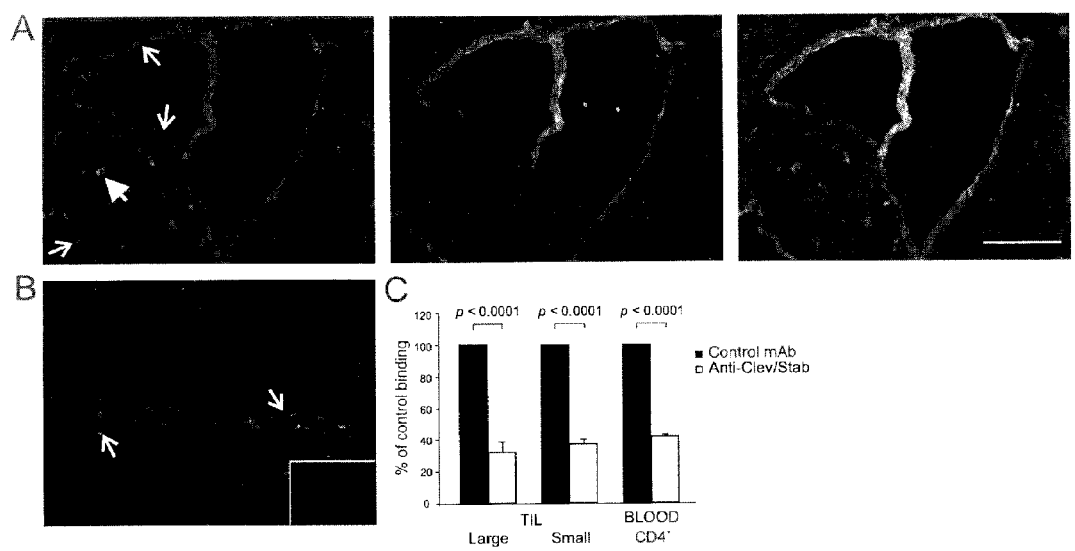
FIG. 10. Expression of Clever-1/Stabilin-1 is induced on tumor vasculature in melanoma, where it binds tumor infiltrating leukocytes and peripheral blood CD4 positive cells. (A) Two-color staining of Clever-1/Stabilin-1 with biotinylated 1.26 antibody (left panel) and PV-1 with MECA-32 antibody (middle panel) identifying the tumor vessels. A merger of the stainings with 1.26 and Meca-32 is shown on the right panel. The vessels are pointed out by thin arrows in the left panel and a type 2 macrophage (positive for Clever-1/Stabilin-1) is pointed out by a thick arrow in the left panel. Bar 100 µm (B) Vascular positivity was confirmed with another monoclonal antibody (9-11) against Clever-1/Stabilin-1 (N-terminal 3 kb fragment). Staining with a negative control antibody is shown in the inset. (C) Clever-1/Stabilin-1 on vasculature mediates binding of tumor infiltrating leukocytes. Binding of large and small tumor infiltrating leukocytes (TIL) as well as CD4 positive cells from the blood to vessels in melanomas obtained from mice treated in vivo with anti-Clever-1/Stabilin-1 (n=3) or control antibody (n=3) was analyzed using ex vivo frozen section assays. The results are presented as mean %±SEM of binding obtained from melanomas of mice treated with the control antibody (by definition 100%).

To find a mechanism behind the reduced number of type 2 macrophages in the tumors we tested, whether the entrance of them or their precursors becomes inhibited during the antibody therapy. First, we analyzed Clever-1/Stablin-1 expression on tumor vasculature. Majority of the vessels within the tumor are enlarged with widely open lumen and unlike normal flat walled vessels they express Clever-1/Stabilin-1. This expression was confirmed using two different antibodies against Clever-1/Stabilin-1 (FIG. 10, A and B). Next, we collected tumors from both anti-Clever-1/Stabilin-1 and control antibody treated animals and tested binding of tumor infiltrating leukocytes and peripheral blood CD4 positive T cells to vessels in those tumors ex vivo. Both tumor infiltrating large leukocytes consisting from macrophages and myeloid cells and tumor infiltrating small lymphocytes bound poorly to tumor vessels of Clever-1/Stabilin-1 treated animals. Also adhesion of CD4 positive blood lymphocytes was reduced (FIG. 10 C). These findings show that Clever-1 blocking therapy prevents monocytes/macrophages and lymphocytes from binding to the vascular system of the tumor. As a result, the development of type 3 macrophages is reduced. Without Clever-1 blocking, type 3 macrophages originating from monocytes entering from the blood stream, will develop and differentiate in the tumor tissue.

Fetomaternal Tolerance:

Expression of Clever-1 in Placenta.

Figure 6:
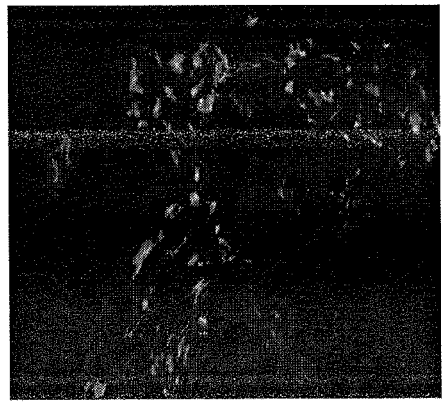
FIG. 6. Expression of Clever-1 in placenta. Frozen sections placenta were stained with anti-Clever-1 antibody (3-372), anti-CD14 (as a macrophage marker) and with negative control antibodies followed appropriate second stage reagents.
Figure 6:
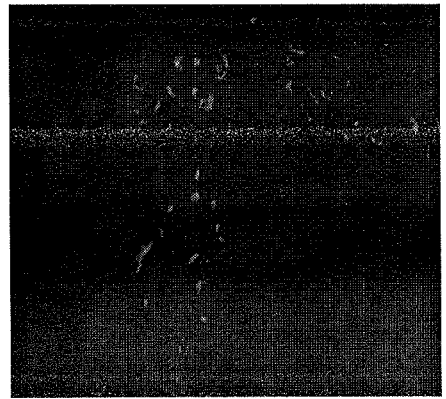
Figure 6:
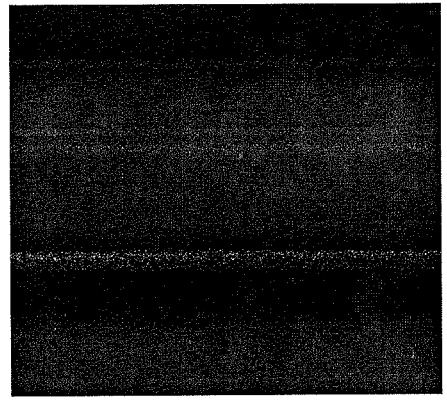
Figure 6:
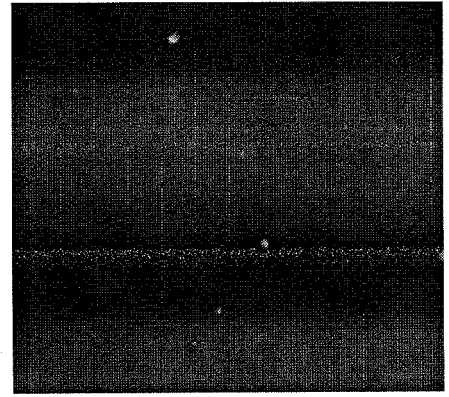

When normal placentas (at term) were immunohistochemically stained for Clever-1, many brightly positive leukocytes were found (FIG. 6). Multicolor FACS analyses further showed that placental NK cells were Clever-1 negative, whereas most CD14 positive macrophages expressed Clever-1 (data not shown).

Expression of Clever-1 in Blood.

Figure 7:
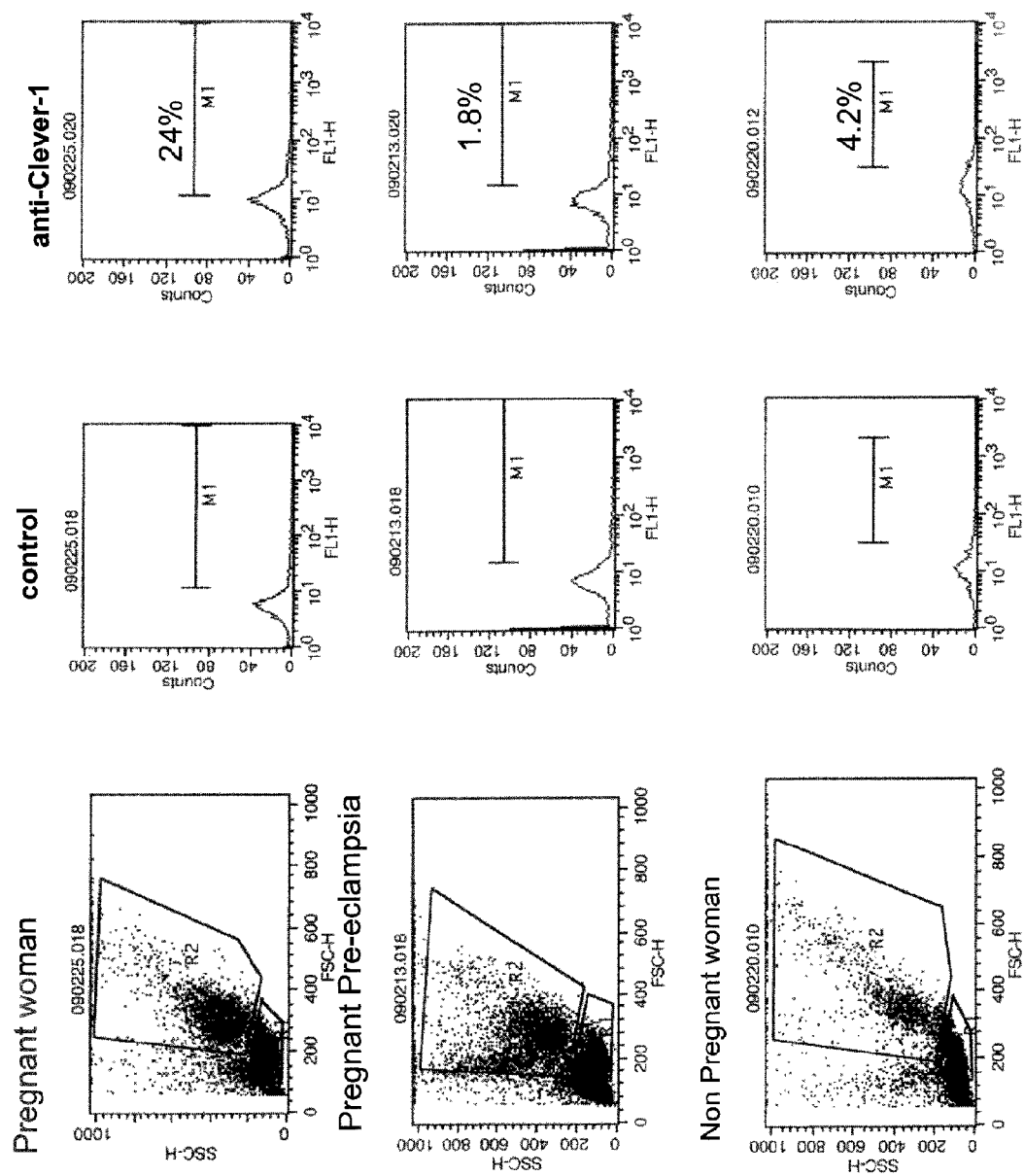
FIG. 7. Cell-surface expression of Clever-1 in blood monocytes during normal pregnancy. Peripheral blood mononuclear cells were isolated from normal, non-pregnant volunteers, from normal pregnant women and from a pregnant women with a mild pre-eclampsia. The mononuclear cells were separated using Ficoll gradient centrifugations and stained with anti-Clever-1 and the control antibody (both at 10 µg/ml), and FITC-conjugated anti-mouse Ig. The cells were analyzed using FACS. The cell populations (R2) analyzed are shown on the left panels with forward and side scatters. In the histograms the fluorescence intensity is in a logarithmic scale on the x axis and relative number of cells on y axis. The percentages shown on the right panels are obtained by deducting the percentage of the positive cells stained with the negative control antibody (=background).

Clever-1 was practically absent or expression was very low on the surface of blood mononuclear leukocytes in healthy individuals tested (FIG. 7). In contrast, pregnant women had clearly detectable levels of Clever-1 on the surface of blood monocytes. Clever-1 was found at all tested time points of pregnancy (weeks 12-38). Interestingly, one individual suffering from a mild pre-eclampsia had no detectable Clever-1 on the surface of the monocytes (FIG. 7).

Expression of Clever-1 can be Upregulated by Interleukin-4 and Dexamethasone and Inhibited by siRNA.

Figure 8:
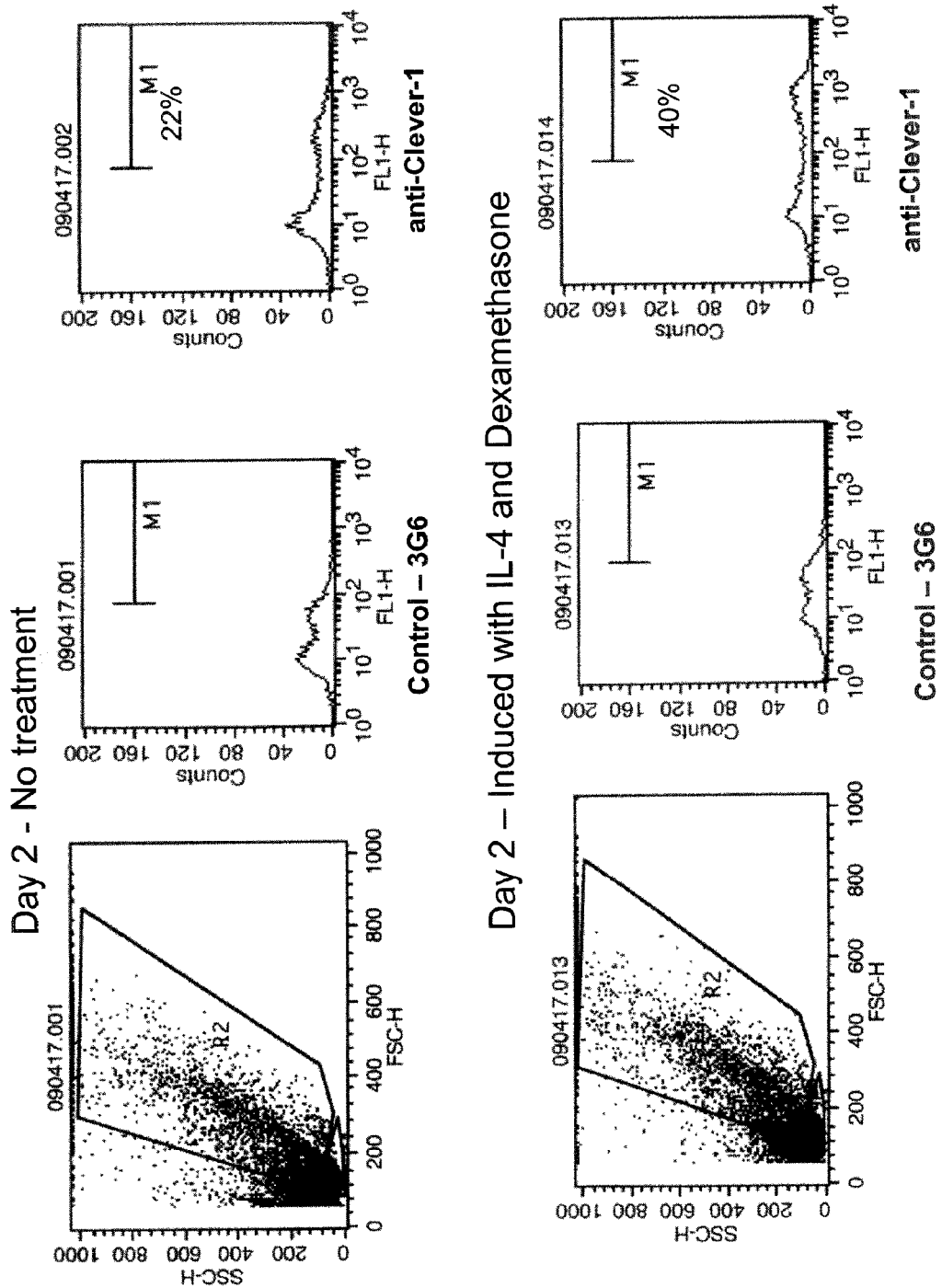
FIG. 8. Interleukin-4 and dexamethasone induce Clever-1 expression in placental macrophages. The forward and side scatters of the cells (R2) analyzed are shown without and with IL-4 and dexmethasone induction (2-days incubation). In the histograms the fluorescence intensity is in a logarithmic scale on the x axis and relative number of cells on y axis. The percentages shown on the right panels are obtained by deducting the percentage of the positive cells stained with the negative control antibody (=background).
Figure 9:
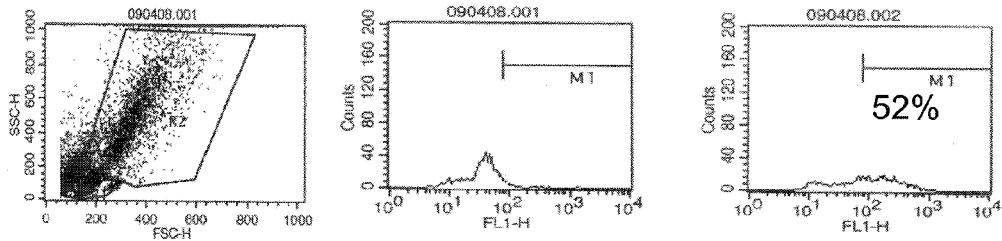
FIG. 9. Clever-1 expression can be downregulated by siRNA treatment. The treatments with a single siRNA species and pooled siRNAs targeting Clever-1 were used. Untreated and treatment with control siRNA are shown as comparison. The forward and side scatters of the cells (R2) analyzed are shown after indicated treatments. In the histograms the fluorescence intensity is in a logarithmic scale on the x axis and relative number of cells on y axis. The percentages shown on the right panels are obtained by deducting the percentage of the positive cells stained with the negative control antibody (=background).
Figure 9:
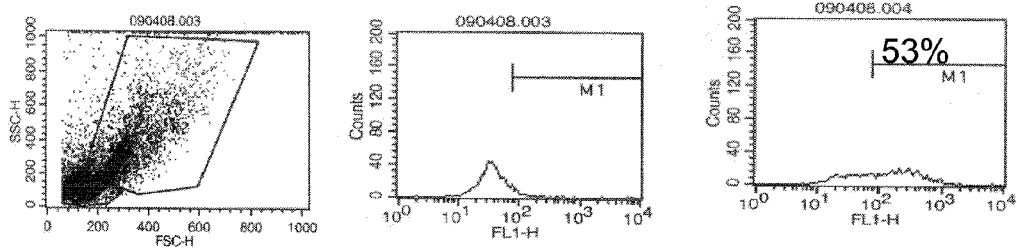
Figure 9:
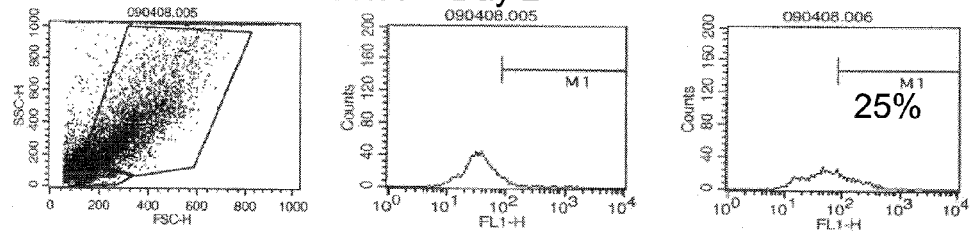
Figure 9:
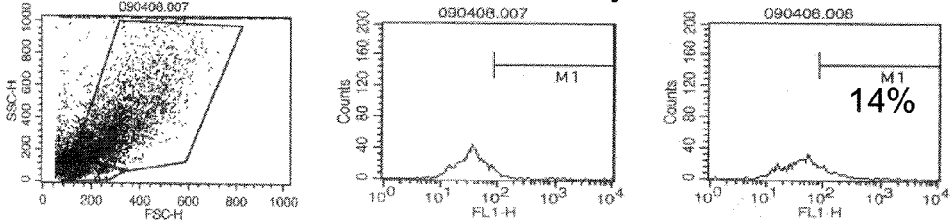

Two days incubation of placental monocytes with interleukin-4 and dexamethasone increases percentage of Clever-1 positive macrophages (FIG. 8). In contrast, the expression can be inhibited with Clever-1 specific siRNA but not with control siRNAs (FIG. 9).

Anti-Clever-1 Antibodies Interfere with Normal Pregnancy in Mice.

Mice were treated with a function blocking anti-mouse Clever-1 antibody or with an isotype-matched control antibody starting from day 1 of pregnancy. The treatments were given intravenously (100 μg mAb/injection) every third day until the delivery. When the mice gave birth, the litter-size was smaller in the mice treated with the anti-Clever-1 antibody when compared to the controls (in control 19 pups and in anti-Clever-1 treated mice 10 pups, n=3 mothers in both groups).

Discussion

Antitumor Effect:

Our work shows that anti-Clever-1 antibody therapy targets a unique subset of suppressive macrophages present in the tumors and leads to reduction in the number of regulatory T cells. Importantly, the antibody treatment does not markedly dampen immune response to the various antigens tested. Although the work has been performed using melanoma as a tumor model, our preliminary experiments with EL-4 lymphoma model indicate that the findings reported in this work are not restricted to melanoma.

Only few molecules present on afferent lymphatics such as macrophage mannose receptor, sphingosine-1-phosphate receptor and CCL21 have been shown to mediate lymphocyte traffic via afferent lymphatic vessels (Marttila-Ichihara, F. et al. *Blood* 112:64-72). Among those Clever-1 is the first one, which is now shown to be involved in and druggable also at the suppressive arm of the anti-cancer immune response.

Tumor associated macrophages differentiate to type 2 macrophages within the tumor environment from the incoming blood monocytes (24). Direct cell-to-cell contact may be required for the differentiation, because peritoneal macrophages (outside the tumor) did not become MR positive in the presence of melanoma within the peritoneal cavity in our experiments (data not shown). About 65% of the MR positive type 2 tumor macrophages express Clever-1. Interestingly, anti-Clever-1 antibody treatment diminished both the number of MR+/Clever-1+ and MR+/Clever-1-macrophages. Presence of MR+/Clever-1+ macrophages within the tumor after the antibody therapy suggests that the antibody does not lead to complement mediated killing of these cells. Reduction of the number of MR+/Clever-1-macrophages, on the other hand, may indicate that also these cells express low levels of Clever-1 and targeting of Clever-1 prevents differentiation of these cells. Alternatively, inhibition of Clever-1 could potentially lead to changes in SPARC content within the tumor limiting the number of suppressive macrophages despite their Clever-1 expression status. SPARC that is endocytosed by Clever-1 has also been demonstrated to be an important component controlling tumor growth and dissemination in several types of cancer (Said, N. et al. *Mol. Cancer. Res.* 5:1015-1030; Chlenski, A. et al. *Cancer Res.* 62:7357-7363; Chlenski, A. et al. *Int. J. Cancer* 118:310-316 and Brekken, R. A. et al. *J. Clin. Invest.* 111:487-495) and could also be regulating the tumor growth in our setting.

The role vascular Clever-1 in the entrance of blood borne monocytes into the melanoma may be ruled out, because the blood vasculature of the B16 melanoma does not express Clever-1. Theoretically it is also possible that Clever-1 on monocytes/macrophages is involved in their entrance from the blood into the primary tumors and antibody therapy inhibits that function.

Type 2 macrophages secrete IL-10 that is immunosuppressive and various chemokines, especially CCL17 and CCL22 which attract CCR4 positive regulatory T cells (Sica, A. et al., *Cancer Lett.* 267:204-215). The reduction of regulatory T cells observed in our work can therefore, may be considered as a consequence of the reduction of type 2 macrophages, especially those expressing Clever-1 i.e type 3 macrophages. Their diminished number and functional capacity may also lower antigen specific tumor cell suppression and the over all immune balance switches from pro-tumoral to anti-tumoral.

Importantly, despite the antibody therapy was effective in the tumor treatment, it did not markedly diminish the immune response against various types of antigens. Reasons behind this may be that the antigens get into the lymph nodes in sufficient quantities to create immune response. Moreover, although the therapy presumably reduces lymphocyte trafficking into and out from the lymph node undergoing the immune response, it does not significantly alter the balance between the entrance of lymphocytes via HEV and their exit from the lymph nodes. Antibodies once created seem to circulate independently of Clever-1 in the body. Remarkably, the macrophages within the lymph nodes during the immune response remained Clever-1 negative although many of them brightly expressed MR. This indicates that MR positive macrophages within the tumors and lymph nodes undergoing the immune response belong to different subtypes. This may also explain, why the antibody therapy targeting Clever-1 during immunization does not have any effect on the number of MR positive macrophages and regulatory T cells.

In summary, our results indicate that Clever-1 is involved in different control points determining cancer growth and dissemination. As the successful treatment of cancer patients frequently requires different combinations of drugs, anti-Clever-1 antibody or another Clever-1 antagonist may be a beneficial addition into the armamentarium used to fight against cancer.

Fetomaternal Tolerance:

We report here that a very prominent population of Clever-1 positive macrophages is present in human placenta. Moreover, Clever-1 is found on the surface of circulating blood monocytes in normal pregnant women, but not (or in very low numbers) in age- and sex-matched control persons. However, in a pre-eclamptic patient, induction of Clever-1 was not seen on the blood monocytes. Finally, an anti-Clever-1 antibody treatment during the course of pregnancy diminished litter-sizes in mice. Together these data suggest that Clever-1 positive cell population is immune suppressive, and that it contributes to the induction of normal tolerance during the pregnancy.

Clever-1 is expressed on a subpopulation of type 2 macrophages in humans and mice. Type 2 macrophages have been shown to be immune suppressing in multiple experimental settings in mice. However, since Clever-1 is not expressed in all type 2 macrophages (normally defined as macrophage mannose receptor positive cells), we propose that a subpopulation of these cells (type 3 macrophages) can be further identified based on Clever-1 expression.

We have shown that type 3 macrophages are normally induced in the placenta and blood circulation during pregnancy. It is known that the induction of Clever-1 can be seen in normal blood monocytes (non-pregnant persons) through stimulation with immune suppressing molecules such as interleukin-4, interleukin-13 or dexamethasone. Probably these, or other anti-inflammatory molecules and steroid hormones, are responsible for Clever-1 induction during pregnancy. We propose that type 3 macrophages are immune suppressing in nature and serve to maintain feto-maternal tolerance in vivo.

Failure to induce Clever-1 in pregnancy may lead to loss of tolerance and manifestations of feto-maternal incompatibility. In early pregnancy this may manifest as spontaneous abortions, and later as conditions like pre-eclampsia. Therefore, induction of Clever-1 on blood monocytes may reflect the level of immune tolerance in the mother, and be useful for early detection of pre-eclampsia. Moreover, therapeutic induction of Clever-1 expressing type 3 macrophages by agents such as interleukins or steroids may be beneficial in boosting tolerance during the pregnancy.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method of treating cancer by reducing the size of malignant tumor and/or by reducing malignant tumor growth in an individual comprising administering to an individual in need thereof an agent which modulates a Clever-1 receptor on a type 3 macrophage cell, wherein the agent is capable of counteracting the influence of or down-regulating the expression of a Clever-1 protein, wherein the agent is an antagonist antibody which is administered intra-tumorally, wherein the antagonistic antibody is monoclonal antibody 3-266 (DSM ACC2510) or monoclonal antibody 3-372 (DSM ACC2520).

2. The method according to claim 1, wherein the cancer is a sarcoma or a carcinoma, especially melanoma or lymphoma.

* * * * *

UNITED STATES PATENT AND TRADEMARK OFFICE
CERTIFICATE OF CORRECTION

PATENT NO. : 8,722,045 B2  
APPLICATION NO. : 13/262088  
DATED : May 13, 2014  
INVENTOR(S) : Sirpa Jalkanen et al.

Page 1 of 1

It is certified that error appears in the above-identified patent and that said Letters Patent is hereby corrected as shown below:

*In the Specification*

Col. 6, line 36: "ACC2590" should be -- ACC2520 --

*In the Claims*

Claim 1, Col. 34, line 16: "ACC2510" should be -- ACC2519 --

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 7879
<212> TYPE: DNA
<213> ORGANISM: Homo sapiens
<220> FEATURE:
<221> NAME/KEY: exon
<222> LOCATION: (31)..(7740)

<400> SEQUENCE: 1
actctgtcct ggacagcgtg cccaccagcc atg gcg ggg ccc cgg ggc ctc ctc         54
                                 Met Ala Gly Pro Arg Gly Leu Leu
                                  1               5 cca ctc tgc ctc ctg gcc ttc tgc ctg gca ggc ttc agc ttc gtc agg        102
Pro Leu Cys Leu Leu Ala Phe Cys Leu Ala Gly Phe Ser Phe Val Arg
     10                  15                  20 ggg cag gtg ctg ttc aaa ggc tgt gat gtg aaa acc acg ttt gtc act        150
Gly Gln Val Leu Phe Lys Gly Cys Asp Val Lys Thr Thr Phe Val Thr
 25                  30                  35                  40 cat gta ccc tgc acc tcg tgc gcg gcc atc aag aag cag acg tgt ccc        198
His Val Pro Cys Thr Ser Cys Ala Ala Ile Lys Lys Gln Thr Cys Pro
                 45                  50                  55 tca ggc tgg ctg cgg gag ctc ccg gat cag ata acc cag gac tgc cgc        246
Ser Gly Trp Leu Arg Glu Leu Pro Asp Gln Ile Thr Gln Asp Cys Arg
             60                  65                  70 tac gaa gta cag ctg ggg ggc tct atg gtg tcc atg agc ggc tgc aga        294
Tyr Glu Val Gln Leu Gly Gly Ser Met Val Ser Met Ser Gly Cys Arg
         75                  80                  85
```

| | |
|---|---|
| cgg aag tgc cgg aag caa gtg gtg cag aag gcc tgc tgc cct ggc tac<br>Arg Lys Cys Arg Lys Gln Val Val Gln Lys Ala Cys Cys Pro Gly Tyr<br>90                         95                       100 | 342 |
| tgg ggt tcc cgg tgc cat gaa tgc cct ggg ggc gct gag acc cca tgc<br>Trp Gly Ser Arg Cys His Glu Cys Pro Gly Gly Ala Glu Thr Pro Cys<br>105                     110                     115                  120 | 390 |
| aat ggc cac ggg acc tgc ttg gat ggc atg gac agg aat ggg acc tgt<br>Asn Gly His Gly Thr Cys Leu Asp Gly Met Asp Arg Asn Gly Thr Cys<br>                       125                     130                     135 | 438 |
| gtg tgc cag gaa aac ttc cgc ggc tca gcc tgc cag gag tgc caa gac<br>Val Cys Gln Glu Asn Phe Arg Gly Ser Ala Cys Gln Glu Cys Gln Asp<br>                      140                     145                     150 | 486 |
| ccc aac cgg ttc ggg cct gac tgc caa tcg gtg tgc agc tgt gtg cac<br>Pro Asn Arg Phe Gly Pro Asp Cys Gln Ser Val Cys Ser Cys Val His<br>               155                     160                     165 | 534 |
| gga gtg tgc aac cat ggg cca cgt ggg gat gga agc tgc ctg tgc ttt<br>Gly Val Cys Asn His Gly Pro Arg Gly Asp Gly Ser Cys Leu Cys Phe<br>          170                     175                     180 | 582 |
| gct gga tac act ggc ccc cac tgt gat caa gag ctg ccc gtc tgc cag<br>Ala Gly Tyr Thr Gly Pro His Cys Asp Gln Glu Leu Pro Val Cys Gln<br>185                       190                     195                  200 | 630 |
| gag ctg cgc tgt ccc cag aac acc cag tgc tcc gca gag gct ccc agc<br>Glu Leu Arg Cys Pro Gln Asn Thr Gln Cys Ser Ala Glu Ala Pro Ser<br>                      205                     210                     215 | 678 |
| tgc agg tgc ctg ccc ggc tac aca cag cag ggc agt gaa tgc cga gcc<br>Cys Arg Cys Leu Pro Gly Tyr Thr Gln Gln Gly Ser Glu Cys Arg Ala<br>               220                     225                     230 | 726 |
| ccc aac ccc tgc tgg cca tca ccc tgc tca ctg ctg gcc cag tgc tcg<br>Pro Asn Pro Cys Trp Pro Ser Pro Cys Ser Leu Leu Ala Gln Cys Ser<br>          235                     240                     245 | 774 |
| gtg agc ccc aag ggg cag gct cag tgt cac tgc cct gag aac tac cat<br>Val Ser Pro Lys Gly Gln Ala Gln Cys His Cys Pro Glu Asn Tyr His<br>250                       255                     260 | 822 |
| ggc gat ggg atg gtg tgt ctg ccc aag gac cca tgc act gac aac ctt<br>Gly Asp Gly Met Val Cys Leu Pro Lys Asp Pro Cys Thr Asp Asn Leu<br>265                       270                     275                  280 | 870 |
| ggt ggc tgc ccc agc aac tct act ttg tgt gtg tac cag aag ccg ggc<br>Gly Gly Cys Pro Ser Asn Ser Thr Leu Cys Val Tyr Gln Lys Pro Gly<br>                      285                     290                     295 | 918 |
| cag gcc ttc tgc acc tgc cgg cca ggc ctg gtc agc atc aac agc aac<br>Gln Ala Phe Cys Thr Cys Arg Pro Gly Leu Val Ser Ile Asn Ser Asn<br>               300                     305                     310 | 966 |
| gct tct gcg ggc tgc ttc gcc ttc tgc tcc ccc ttc tcc tgc gac cgg<br>Ala Ser Ala Gly Cys Phe Ala Phe Cys Ser Pro Phe Ser Cys Asp Arg<br>          315                     320                     325 | 1014 |
| tct gcc act tgc cag gtg acc gct gat ggg aag acc agc tgt gtg tgc<br>Ser Ala Thr Cys Gln Val Thr Ala Asp Gly Lys Thr Ser Cys Val Cys<br>330                       335                     340 | 1062 |
| agg gaa agc gag gtg ggg gat ggg cgt gcc tgc tac gga cac ctg ctc<br>Arg Glu Ser Glu Val Gly Asp Gly Arg Ala Cys Tyr Gly His Leu Leu<br>345                       350                     355                  360 | 1110 |
| cac gag gtg cag aag gcc acg cag aca ggc cgg gtg ttc ctg cag ctg<br>His Glu Val Gln Lys Ala Thr Gln Thr Gly Arg Val Phe Leu Gln Leu<br>                      365                     370                     375 | 1158 |
| agg gtc gcc gtg gcc atg atg gac cag ggc tgc cgg gaa atc ctt acc<br>Arg Val Ala Val Ala Met Met Asp Gln Gly Cys Arg Glu Ile Leu Thr<br>               380                     385                     390 | 1206 |
| aca gcg ggc cct ttc acc gtg ctg gtg cca tcc gtc tcc tcc ttc tcc<br>Thr Ala Gly Pro Phe Thr Val Leu Val Pro Ser Val Ser Ser Phe Ser<br>          395                     400                     405 | 1254 |

```
tcc agg acc atg aat gca tcc ctt gcc cag cag ctc tgt aga cag cac    1302
Ser Arg Thr Met Asn Ala Ser Leu Ala Gln Gln Leu Cys Arg Gln His
    410                 415                 420 atc atc gca ggg cag cac atc ctg gag gac aca agg acc caa caa aca    1350
Ile Ile Ala Gly Gln His Ile Leu Glu Asp Thr Arg Thr Gln Gln Thr
425                 430                 435                 440 cga agg tgg tgg acg ctg gcc ggg cag gag atc acc gtc acc ttt aac    1398
Arg Arg Trp Trp Thr Leu Ala Gly Gln Glu Ile Thr Val Thr Phe Asn
                445                 450                 455 caa ttc acg aaa tac tcc tac aag tac aaa gac cag ccc cag cag acg    1446
Gln Phe Thr Lys Tyr Ser Tyr Lys Tyr Lys Asp Gln Pro Gln Gln Thr
        460                 465                 470 ttc aac atc tac aag gcc aac aac ata gca gct aat ggc gtc ttc cac    1494
Phe Asn Ile Tyr Lys Ala Asn Asn Ile Ala Ala Asn Gly Val Phe His
            475                 480                 485 gtg gtc act ggc ctg cgg tgg cag gcc ccc tct ggg acc cct ggg gat    1542
Val Val Thr Gly Leu Arg Trp Gln Ala Pro Ser Gly Thr Pro Gly Asp
490                 495                 500 ccc aag aga act atc gga cag atc ctc gcc tct acc gag gcc ttc agc    1590
Pro Lys Arg Thr Ile Gly Gln Ile Leu Ala Ser Thr Glu Ala Phe Ser
505                 510                 515                 520 cgc ttt gaa acc atc ctg gag aac tgt ggg ctg ccc tcc atc ctg gac    1638
Arg Phe Glu Thr Ile Leu Glu Asn Cys Gly Leu Pro Ser Ile Leu Asp
                525                 530                 535 gga cct ggg ccc ttc aca gtc ttt gcc cca agc aat gag gct gtg gac    1686
Gly Pro Gly Pro Phe Thr Val Phe Ala Pro Ser Asn Glu Ala Val Asp
        540                 545                 550 agc ttg cgt gac ggc cgc ctg atc tac ctc ttc aca gcg ggt ctc tct    1734
Ser Leu Arg Asp Gly Arg Leu Ile Tyr Leu Phe Thr Ala Gly Leu Ser
            555                 560                 565 aaa ctg cag gag ttg gtg cgg tac cac atc tac aac cac ggc cag ctg    1782
Lys Leu Gln Glu Leu Val Arg Tyr His Ile Tyr Asn His Gly Gln Leu
570                 575                 580 acc gtt gag aag ctc atc tcc aag ggt cgg atc ctc acc atg gcg aac    1830
Thr Val Glu Lys Leu Ile Ser Lys Gly Arg Ile Leu Thr Met Ala Asn
585                 590                 595                 600 cag gtc ctg gct gtg aac att tct gag gag ggg cgc atc ctg ctg gga    1878
Gln Val Leu Ala Val Asn Ile Ser Glu Glu Gly Arg Ile Leu Leu Gly
                605                 610                 615 ccc gag ggg gtc ccg ctg cag agg gta gac gtg atg gcc gcc aat ggt    1926
Pro Glu Gly Val Pro Leu Gln Arg Val Asp Val Met Ala Ala Asn Gly
        620                 625                 630 gtg atc cac atg ctg gac ggc atc ctg ctg ccc ccg acc atc ctg ccc    1974
Val Ile His Met Leu Asp Gly Ile Leu Leu Pro Pro Thr Ile Leu Pro
            635                 640                 645 atc ctg ccc aag cac tgc agc gag gag cag cac aag att gtg gcg ggc    2022
Ile Leu Pro Lys His Cys Ser Glu Glu Gln His Lys Ile Val Ala Gly
650                 655                 660 tcc tgt gtg gac tgc caa gcc ctg aac acc agc acg tgt ccc ccc aac    2070
Ser Cys Val Asp Cys Gln Ala Leu Asn Thr Ser Thr Cys Pro Pro Asn
665                 670                 675                 680 agt gtg aag ctg gac atc ttc ccc aag gag tgt gtc tac atc cat gac    2118
Ser Val Lys Leu Asp Ile Phe Pro Lys Glu Cys Val Tyr Ile His Asp
                685                 690                 695 cca acg ggg ctc aat gtg cta aag aag ggc tgt gcc agc tac tgc aac    2166
Pro Thr Gly Leu Asn Val Leu Lys Lys Gly Cys Ala Ser Tyr Cys Asn
        700                 705                 710 caa acc atc atg gaa caa ggc tgc tgc aaa ggt ttt ttc ggg cct gac    2214
Gln Thr Ile Met Glu Gln Gly Cys Cys Lys Gly Phe Phe Gly Pro Asp
            715                 720                 725
```

| | |
|---|---|
| tgc acg cag tgt cct ggg ggc ttc tcc aac ccc tgc tat ggc aaa ggc<br>Cys Thr Gln Cys Pro Gly Gly Phe Ser Asn Pro Cys Tyr Gly Lys Gly<br>730                         735                    740 | 2262 |
| aat tgc agt gat ggg atc cag ggc aat ggg gcc tgc ctc tgc ttc cca<br>Asn Cys Ser Asp Gly Ile Gln Gly Asn Gly Ala Cys Leu Cys Phe Pro<br>745                       750                     755                  760 | 2310 |
| gac tac aag ggc atc gcc tgc cac atc tgc tcg aac cca aac aag cat<br>Asp Tyr Lys Gly Ile Ala Cys His Ile Cys Ser Asn Pro Asn Lys His<br>                            765                   770                   775 | 2358 |
| gga gag caa tgc cag gaa gac tgc ggc tgt gtc cat ggt ctc tgc gac<br>Gly Glu Gln Cys Gln Glu Asp Cys Gly Cys Val His Gly Leu Cys Asp<br>                 780                   785                     790 | 2406 |
| aac cgc cca ggc agt ggg ggg gtg tgc cag cag ggc acg tgt gcc cct<br>Asn Arg Pro Gly Ser Gly Gly Val Cys Gln Gln Gly Thr Cys Ala Pro<br>795                       800                     805 | 2454 |
| ggc ttc agt ggc cgg ttc tgc aac gag tcc atg ggg gac tgt ggg ccc<br>Gly Phe Ser Gly Arg Phe Cys Asn Glu Ser Met Gly Asp Cys Gly Pro<br>         810                   815                   820 | 2502 |
| aca ggg ctg gcc cag cac tgc cac ctg cat gcc cgc tgt gtt agc cag<br>Thr Gly Leu Ala Gln His Cys His Leu His Ala Arg Cys Val Ser Gln<br>825                       830                     835                  840 | 2550 |
| gag ggt gtt gcc aga tgt cgc tgt ctt gat ggc ttt gag ggt gat ggc<br>Glu Gly Val Ala Arg Cys Arg Cys Leu Asp Gly Phe Glu Gly Asp Gly<br>                       845                   850                   855 | 2598 |
| ttc tcc tgc aca cct agc aac ccc tgc tcc cac ccg gac cgt gga ggc<br>Phe Ser Cys Thr Pro Ser Asn Pro Cys Ser His Pro Asp Arg Gly Gly<br>               860                     865                   870 | 2646 |
| tgc tca gag aat gct gag tgt gtc cct ggg tcc ctg ggc acc cac cac<br>Cys Ser Glu Asn Ala Glu Cys Val Pro Gly Ser Leu Gly Thr His His<br>                     875                   880                   885 | 2694 |
| tgc aca tgc cac aaa ggc tgg agt ggg gat ggc cgc gtc tgt gtg gct<br>Cys Thr Cys His Lys Gly Trp Ser Gly Asp Gly Arg Val Cys Val Ala<br>890                       895                     900 | 2742 |
| att gac gag tgt gag ctg gac gtg aga ggt ggc tgc cac acc gat gcc<br>Ile Asp Glu Cys Glu Leu Asp Val Arg Gly Gly Cys His Thr Asp Ala<br>905                       910                     915                  920 | 2790 |
| ctc tgc agc tat gtg ggc ccc ggg cag agc cga tgc acc tgc aag ctg<br>Leu Cys Ser Tyr Val Gly Pro Gly Gln Ser Arg Cys Thr Cys Lys Leu<br>                     925                   930                   935 | 2838 |
| ggc ttt gcc ggg gat ggc tac cag tgc agc ccc atc gac ccc tgc cgg<br>Gly Phe Ala Gly Asp Gly Tyr Gln Cys Ser Pro Ile Asp Pro Cys Arg<br>               940                     945                   950 | 2886 |
| gca ggc aat ggc ggc tgc cac ggc ctg gcc acc tgc cgg gca gtg ggg<br>Ala Gly Asn Gly Gly Cys His Gly Leu Ala Thr Cys Arg Ala Val Gly<br>                   955                   960                   965 | 2934 |
| gga ggt cag cgg gtc tgc acg tgc ccc cct ggc ttt ggg ggt gat ggc<br>Gly Gly Gln Arg Val Cys Thr Cys Pro Pro Gly Phe Gly Gly Asp Gly<br>970                       975                     980 | 2982 |
| ttc agc tgt tat gga gac atc ttc cgg gag ctg gag gca aat gcc cac<br>Phe Ser Cys Tyr Gly Asp Ile Phe Arg Glu Leu Glu Ala Asn Ala His<br>985                       990                     995                 1000 | 3030 |
| ttc tcc atc ttc tac caa tgg ctt aag agt gcc ggc atc acg ctt<br>Phe Ser Ile Phe Tyr Gln Trp Leu Lys Ser Ala Gly Ile Thr Leu<br>                   1005                 1010                1015 | 3075 |
| cct gcc gac cgc cga gtc aca gcc ctg gtg ccc tcc gag gct gca<br>Pro Ala Asp Arg Arg Val Thr Ala Leu Val Pro Ser Glu Ala Ala<br>                   1020                 1025                1030 | 3120 |
| gtc cgt cag ctg agc ccc gag gac cga gct ttc tgg ctg cag cca<br>Val Arg Gln Leu Ser Pro Glu Asp Arg Ala Phe Trp Leu Gln Pro<br>                   1035                 1040                1045 | 3165 |

```
agg acg ctg ccg aac ctg gtc agg gcc cat ttt ctc cag ggt gcc      3210
Arg Thr Leu Pro Asn Leu Val Arg Ala His Phe Leu Gln Gly Ala
            1050                1055                1060 ctc ttc gag gag gag ctg gcc cgg ctg ggt ggg cag gaa gtg gcc      3255
Leu Phe Glu Glu Glu Leu Ala Arg Leu Gly Gly Gln Glu Val Ala
            1065                1070                1075 acc ctg aac ccc acc aca cgc tgg gag att cgc aac att agt ggg      3300
Thr Leu Asn Pro Thr Thr Arg Trp Glu Ile Arg Asn Ile Ser Gly
            1080                1085                1090 agg gtc tgg gtg cag aat gcc agc gtg gat gtg gct gac ctc ctt      3345
Arg Val Trp Val Gln Asn Ala Ser Val Asp Val Ala Asp Leu Leu
            1095                1100                1105 gcc acc aac ggt gtc cta cac atc ctc agc cag gtc tta ctc ccc      3390
Ala Thr Asn Gly Val Leu His Ile Leu Ser Gln Val Leu Leu Pro
            1110                1115                1120 ccc cga ggg gat gtg ccc ggt ggg cag ggg ttg ctg cag cag ctg      3435
Pro Arg Gly Asp Val Pro Gly Gly Gln Gly Leu Leu Gln Gln Leu
            1125                1130                1135 gac ttg gtg cct gcc ttc agc ctc ttc cgg gaa ttg ctg cag cac      3480
Asp Leu Val Pro Ala Phe Ser Leu Phe Arg Glu Leu Leu Gln His
            1140                1145                1150 cat ggg ttg gtg ccc cag att gag gct gcc act gcc tac acc atc      3525
His Gly Leu Val Pro Gln Ile Glu Ala Ala Thr Ala Tyr Thr Ile
            1155                1160                1165 ttt gtg ccc acc aac cgc tcc ctg gag gcc cag ggc aac agc agt      3570
Phe Val Pro Thr Asn Arg Ser Leu Glu Ala Gln Gly Asn Ser Ser
            1170                1175                1180 cac ctg gac gca gac aca gtg cgg cac cat gtg gtc ctg ggg gag      3615
His Leu Asp Ala Asp Thr Val Arg His His Val Val Leu Gly Glu
            1185                1190                1195 gcc ctc tcc atg gaa acc ctg cgg aag ggt gga cac cgc aac tcc      3660
Ala Leu Ser Met Glu Thr Leu Arg Lys Gly Gly His Arg Asn Ser
            1200                1205                1210 ctc ctg ggc cct gcc cac tgg atc gtc ttc tac aac cac agt ggc      3705
Leu Leu Gly Pro Ala His Trp Ile Val Phe Tyr Asn His Ser Gly
            1215                1220                1225 cag cct gag gtg aac cat gtg cca ctg gaa ggc ccc atg ctg gag      3750
Gln Pro Glu Val Asn His Val Pro Leu Glu Gly Pro Met Leu Glu
            1230                1235                1240 gcc cct ggc cgc tcg ctg att ggt ctg tcg ggg gtc ctg acg gtg      3795
Ala Pro Gly Arg Ser Leu Ile Gly Leu Ser Gly Val Leu Thr Val
            1245                1250                1255 ggc tca agt cgc tgc ctg cat agc cac gct gag gcc ctg cgg gag      3840
Gly Ser Ser Arg Cys Leu His Ser His Ala Glu Ala Leu Arg Glu
            1260                1265                1270 aaa tgt gta aac tgc acc agg aga ttc cgc tgc act cag ggc ttc      3885
Lys Cys Val Asn Cys Thr Arg Arg Phe Arg Cys Thr Gln Gly Phe
            1275                1280                1285 cag ctg cag gac aca ccc agg aag agc tgt gtc tac cga tct ggc      3930
Gln Leu Gln Asp Thr Pro Arg Lys Ser Cys Val Tyr Arg Ser Gly
            1290                1295                1300 ttc tcc ttc tcc cgg ggc tgc tct tac aca tgt gcc aag aag atc      3975
Phe Ser Phe Ser Arg Gly Cys Ser Tyr Thr Cys Ala Lys Lys Ile
            1305                1310                1315 cag gtg ccg gac tgc tgc cct ggt ttc ttt ggc acg ctg tgt gag      4020
Gln Val Pro Asp Cys Cys Pro Gly Phe Phe Gly Thr Leu Cys Glu
            1320                1325                1330 cca tgc cca ggg ggt cta ggg ggg gtg tgc tca ggc cat ggg cag      4065
Pro Cys Pro Gly Gly Leu Gly Gly Val Cys Ser Gly His Gly Gln
            1335                1340                1345
```

-continued

| | |
|---|---|
| tgc cag gac agg ttc ctg ggc agc ggg gag tgc cac tgc cac gag<br>Cys Gln Asp Arg Phe Leu Gly Ser Gly Glu Cys His Cys His Glu<br>1350                             1355                          1360 | 4110 |
| ggc ttc cat gga acg gcc tgt gag gtg tgt gag ctg ggc cgc tac<br>Gly Phe His Gly Thr Ala Cys Glu Val Cys Glu Leu Gly Arg Tyr<br>1365                             1370                          1375 | 4155 |
| ggg ccc aac tgc acc gga gtg tgt gac tgt gcc cat ggg ctg tgc<br>Gly Pro Asn Cys Thr Gly Val Cys Asp Cys Ala His Gly Leu Cys<br>1380                             1385                          1390 | 4200 |
| cag gag ggg ctg caa ggg gac gga agc tgt gtc tgt aac gtg ggc<br>Gln Glu Gly Leu Gln Gly Asp Gly Ser Cys Val Cys Asn Val Gly<br>1395                             1400                          1405 | 4245 |
| tgg cag ggc ctc cgc tgt gac cag aaa atc acc agc cct cag tgc<br>Trp Gln Gly Leu Arg Cys Asp Gln Lys Ile Thr Ser Pro Gln Cys<br>1410                             1415                          1420 | 4290 |
| cct agg aag tgc gac ccc aat gcc aac tgc gtg cag gac tcg gcc<br>Pro Arg Lys Cys Asp Pro Asn Ala Asn Cys Val Gln Asp Ser Ala<br>1425                             1430                          1435 | 4335 |
| gga gcc tcc acc tgc gcc tgt gct gcg gga tac tcc ggc aat ggc<br>Gly Ala Ser Thr Cys Ala Cys Ala Ala Gly Tyr Ser Gly Asn Gly<br>1440                             1445                          1450 | 4380 |
| atc ttc tgt tca gag gtg gac ccc tgc gcc cac ggc cat ggg ggc<br>Ile Phe Cys Ser Glu Val Asp Pro Cys Ala His Gly His Gly Gly<br>1455                             1460                          1465 | 4425 |
| tgc tcc cct cat gcc aac tgt acc aag gtg gca cct ggg cag cgg<br>Cys Ser Pro His Ala Asn Cys Thr Lys Val Ala Pro Gly Gln Arg<br>1470                             1475                          1480 | 4470 |
| aca tgc acc tgc cag gat ggc tac atg ggc gac ggg gag ctg tgc<br>Thr Cys Thr Cys Gln Asp Gly Tyr Met Gly Asp Gly Glu Leu Cys<br>1485                             1490                          1495 | 4515 |
| cag gaa att aac agc tgt ctc atc cac cac ggg ggc tgc cac att<br>Gln Glu Ile Asn Ser Cys Leu Ile His His Gly Gly Cys His Ile<br>1500                             1505                          1510 | 4560 |
| cac gcc gag tgc atc ccc act ggc ccc cag cag gtc tcc tgc agc<br>His Ala Glu Cys Ile Pro Thr Gly Pro Gln Gln Val Ser Cys Ser<br>1515                             1520                          1525 | 4605 |
| tgc cgt gag ggt tac agc ggg gat ggc atc cgg acc tgc gag ctc<br>Cys Arg Glu Gly Tyr Ser Gly Asp Gly Ile Arg Thr Cys Glu Leu<br>1530                             1535                          1540 | 4650 |
| ctg gac ccc tgc tct aag aac aat gga gga tgc agc cca tat gcc<br>Leu Asp Pro Cys Ser Lys Asn Asn Gly Gly Cys Ser Pro Tyr Ala<br>1545                             1550                          1555 | 4695 |
| acc tgc aaa agc aca ggg gat ggc cag agg aca tgt acc tgc gac<br>Thr Cys Lys Ser Thr Gly Asp Gly Gln Arg Thr Cys Thr Cys Asp<br>1560                             1565                          1570 | 4740 |
| aca gcc cac acc gtg ggg gac ggc ctc acc tgc cgt gcc cga gtc<br>Thr Ala His Thr Val Gly Asp Gly Leu Thr Cys Arg Ala Arg Val<br>1575                             1580                          1585 | 4785 |
| ggc ctg gag ctc ctg agg gat aag cat gcc tca ttc ttc agc ctc<br>Gly Leu Glu Leu Leu Arg Asp Lys His Ala Ser Phe Phe Ser Leu<br>1590                             1595                          1600 | 4830 |
| cgc ctc ctg gaa tat aag gag ctc aag ggc gat ggg cct ttc acc<br>Arg Leu Leu Glu Tyr Lys Glu Leu Lys Gly Asp Gly Pro Phe Thr<br>1605                             1610                          1615 | 4875 |
| atc ttc gtg ccg cac gca gat cta atg agc aac ctg tcg cag gat<br>Ile Phe Val Pro His Ala Asp Leu Met Ser Asn Leu Ser Gln Asp<br>1620                             1625                          1630 | 4920 |
| gag ctg gcc cgg att cgt gcg cat cgc cag ctg gtg ttt cgc tac<br>Glu Leu Ala Arg Ile Arg Ala His Arg Gln Leu Val Phe Arg Tyr<br>1635                             1640                          1645 | 4965 |

```
cac gtg gtt ggc tgt  cgg cgg ctg cgg agc  gag gac ctg ctg gag            5010
His Val Val Gly Cys  Arg Arg Leu Arg Ser  Glu Asp Leu Leu Glu
            1650                 1655                 1660 cag ggg tac gcc acg  gcc ctc tca ggg cac  cca ctg cgc ttc agc            5055
Gln Gly Tyr Ala Thr  Ala Leu Ser Gly His  Pro Leu Arg Phe Ser
            1665                 1670                 1675 gag agg gag ggc agc  ata tac ctc aat gac  ttc gcg cgc gtg gtg            5100
Glu Arg Glu Gly Ser  Ile Tyr Leu Asn Asp  Phe Ala Arg Val Val
            1680                 1685                 1690 agc agc gac cat gag  gcc gtg aac ggc atc  ctg cac ttc att gac            5145
Ser Ser Asp His Glu  Ala Val Asn Gly Ile  Leu His Phe Ile Asp
            1695                 1700                 1705 cgt gtc ctg ctg ccc  ccc gag gcg ctg cac  tgg gag cct gat gat            5190
Arg Val Leu Leu Pro  Pro Glu Ala Leu His  Trp Glu Pro Asp Asp
            1710                 1715                 1720 gct ccc atc ccg agg  aga aat gtc acc gcc  gcc gcc cag ggc ttc            5235
Ala Pro Ile Pro Arg  Arg Asn Val Thr Ala  Ala Ala Gln Gly Phe
            1725                 1730                 1735 ggt tac aag atc ttc  agc ggc ctc ctg aag  gtg gcc ggc ctc ctg            5280
Gly Tyr Lys Ile Phe  Ser Gly Leu Leu Lys  Val Ala Gly Leu Leu
            1740                 1745                 1750 ccc ctg ctt cga gag  gca tcc cat agg ccc  ttc aca atg ctg tgg            5325
Pro Leu Leu Arg Glu  Ala Ser His Arg Pro  Phe Thr Met Leu Trp
            1755                 1760                 1765 ccc aca gac gcc gcc  ttt cga gct ctg cct  ccg gat cgc cag gcc            5370
Pro Thr Asp Ala Ala  Phe Arg Ala Leu Pro  Pro Asp Arg Gln Ala
            1770                 1775                 1780 tgg ctg tac cat gag  gac cac cgt gac aag  cta gca gcc att ctg            5415
Trp Leu Tyr His Glu  Asp His Arg Asp Lys  Leu Ala Ala Ile Leu
            1785                 1790                 1795 cgg ggc cac atg att  cgc aat gtc gag gcc  ttg gca tct gac ctg            5460
Arg Gly His Met Ile  Arg Asn Val Glu Ala  Leu Ala Ser Asp Leu
            1800                 1805                 1810 ccc aac ctg ggc cca  ctt cga acc atg cat  ggg acc ccc atc tct            5505
Pro Asn Leu Gly Pro  Leu Arg Thr Met His  Gly Thr Pro Ile Ser
            1815                 1820                 1825 ttc tcc tgc agc cga  acg cgg ccc ggt gag  ctc atg gtg ggt gag            5550
Phe Ser Cys Ser Arg  Thr Arg Pro Gly Glu  Leu Met Val Gly Glu
            1830                 1835                 1840 gat gat gct cgc att  gtg cag cgg cac ttg  ccc ttt gag ggt ggc            5595
Asp Asp Ala Arg Ile  Val Gln Arg His Leu  Pro Phe Glu Gly Gly
            1845                 1850                 1855 ctg gcc tat ggc atc  gac cag ctg ctg gag  cca cct ggc ctt ggt            5640
Leu Ala Tyr Gly Ile  Asp Gln Leu Leu Glu  Pro Pro Gly Leu Gly
            1860                 1865                 1870 gct cgc tgt gac cac  ttt gag acc cgg ccc  ctg cga ctg aac acc            5685
Ala Arg Cys Asp His  Phe Glu Thr Arg Pro  Leu Arg Leu Asn Thr
            1875                 1880                 1885 tgc agc atc tgt ggg  ctg gag cca ccc tgt  cct gag ggg tca cag            5730
Cys Ser Ile Cys Gly  Leu Glu Pro Pro Cys  Pro Glu Gly Ser Gln
            1890                 1895                 1900 gag cag ggc agc cct  gag gcc tgc tgg cgc  ttc tac ccg aag ttc            5775
Glu Gln Gly Ser Pro  Glu Ala Cys Trp Arg  Phe Tyr Pro Lys Phe
            1905                 1910                 1915 tgg acg tcc cct ccg  ctg cac tct ttg gga  tta cgc agc gtc tgg            5820
Trp Thr Ser Pro Pro  Leu His Ser Leu Gly  Leu Arg Ser Val Trp
            1920                 1925                 1930 gtc cac ccc agc ctt  tgg ggt agg ccc caa  ggc ctg ggc agg ggc            5865
Val His Pro Ser Leu  Trp Gly Arg Pro Gln  Gly Leu Gly Arg Gly
            1935                 1940                 1945
```

-continued

| | | | | | | | | | | | | | | |
|---|---|---|---|---|---|---|---|---|---|---|---|---|---|---|
| tgc | cac | cgc | aat | tgt | gtc | acc | acc | acc | tgg | aag | ccc | agc | tgc | tgc | 5910 |
| Cys | His | Arg | Asn | Cys | Val | Thr | Thr | Thr | Trp | Lys | Pro | Ser | Cys | Cys | |
| | | | 1950 | | | | | 1955 | | | | | 1960 | | |

| | | | | | | | | | | | | | | |
|---|---|---|---|---|---|---|---|---|---|---|---|---|---|---|
| cct | ggt | cac | tat | ggc | agt | gag | tgc | caa | gct | tgc | cct | ggc | ggc | ccc | 5955 |
| Pro | Gly | His | Tyr | Gly | Ser | Glu | Cys | Gln | Ala | Cys | Pro | Gly | Gly | Pro | |
| | | 1965 | | | | | 1970 | | | | | 1975 | | | |

| | | | | | | | | | | | | | | |
|---|---|---|---|---|---|---|---|---|---|---|---|---|---|---|
| agc | agc | cct | tgt | agt | gac | cgt | ggc | gtg | tgc | atg | gac | ggc | atg | agt | 6000 |
| Ser | Ser | Pro | Cys | Ser | Asp | Arg | Gly | Val | Cys | Met | Asp | Gly | Met | Ser | |
| | | | 1980 | | | | | 1985 | | | | | 1990 | | |

| | | | | | | | | | | | | | | |
|---|---|---|---|---|---|---|---|---|---|---|---|---|---|---|
| ggc | agt | ggg | cag | tgt | ctg | tgc | cgt | tca | ggt | ttt | gct | ggg | aca | gcc | 6045 |
| Gly | Ser | Gly | Gln | Cys | Leu | Cys | Arg | Ser | Gly | Phe | Ala | Gly | Thr | Ala | |
| | | 1995 | | | | | 2000 | | | | | 2005 | | | |

| | | | | | | | | | | | | | | |
|---|---|---|---|---|---|---|---|---|---|---|---|---|---|---|
| tgt | gaa | ctc | tgt | gct | cct | ggt | gcc | ttt | ggg | ccc | cat | tgt | caa | gcc | 6090 |
| Cys | Glu | Leu | Cys | Ala | Pro | Gly | Ala | Phe | Gly | Pro | His | Cys | Gln | Ala | |
| | | | 2010 | | | | | 2015 | | | | | 2020 | | |

| | | | | | | | | | | | | | | |
|---|---|---|---|---|---|---|---|---|---|---|---|---|---|---|
| tgc | cgc | tgc | act | gtg | cat | ggc | cgc | tgt | gat | gag | ggc | ctt | ggg | ggc | 6135 |
| Cys | Arg | Cys | Thr | Val | His | Gly | Arg | Cys | Asp | Glu | Gly | Leu | Gly | Gly | |
| | | 2025 | | | | | 2030 | | | | | 2035 | | | |

| | | | | | | | | | | | | | | |
|---|---|---|---|---|---|---|---|---|---|---|---|---|---|---|
| tct | ggc | tcc | tgc | ttc | tgt | gat | gaa | ggc | tgg | act | ggg | cca | cgc | tgt | 6180 |
| Ser | Gly | Ser | Cys | Phe | Cys | Asp | Glu | Gly | Trp | Thr | Gly | Pro | Arg | Cys | |
| | | | 2040 | | | | | 2045 | | | | | 2050 | | |

| | | | | | | | | | | | | | | |
|---|---|---|---|---|---|---|---|---|---|---|---|---|---|---|
| gag | gtg | caa | ctg | gag | ctg | cag | cct | gtg | tgt | acc | cca | ccc | tgt | gca | 6225 |
| Glu | Val | Gln | Leu | Glu | Leu | Gln | Pro | Val | Cys | Thr | Pro | Pro | Cys | Ala | |
| | | 2055 | | | | | 2060 | | | | | 2065 | | | |

| | | | | | | | | | | | | | | |
|---|---|---|---|---|---|---|---|---|---|---|---|---|---|---|
| ccc | gag | gct | gtg | tgc | cgt | gca | ggc | aac | agc | tgt | gag | tgc | agc | ctg | 6270 |
| Pro | Glu | Ala | Val | Cys | Arg | Ala | Gly | Asn | Ser | Cys | Glu | Cys | Ser | Leu | |
| | | | 2070 | | | | | 2075 | | | | | 2080 | | |

| | | | | | | | | | | | | | | |
|---|---|---|---|---|---|---|---|---|---|---|---|---|---|---|
| ggc | tat | gaa | ggg | gat | ggc | cgc | gtg | tgt | aca | gtg | gca | gac | ctg | tgc | 6315 |
| Gly | Tyr | Glu | Gly | Asp | Gly | Arg | Val | Cys | Thr | Val | Ala | Asp | Leu | Cys | |
| | | 2085 | | | | | 2090 | | | | | 2095 | | | |

| | | | | | | | | | | | | | | |
|---|---|---|---|---|---|---|---|---|---|---|---|---|---|---|
| cag | gac | ggg | cat | ggt | ggc | tgc | agt | gag | cac | gcc | aac | tgt | agc | cag | 6360 |
| Gln | Asp | Gly | His | Gly | Gly | Cys | Ser | Glu | His | Ala | Asn | Cys | Ser | Gln | |
| | | | 2100 | | | | | 2105 | | | | | 2110 | | |

| | | | | | | | | | | | | | | |
|---|---|---|---|---|---|---|---|---|---|---|---|---|---|---|
| gta | gga | aca | atg | gtc | act | tgt | acc | tgc | ctg | ccc | gac | tac | gag | ggt | 6405 |
| Val | Gly | Thr | Met | Val | Thr | Cys | Thr | Cys | Leu | Pro | Asp | Tyr | Glu | Gly | |
| | | 2115 | | | | | 2120 | | | | | 2125 | | | |

| | | | | | | | | | | | | | | |
|---|---|---|---|---|---|---|---|---|---|---|---|---|---|---|
| gat | ggc | tgg | agc | tgc | cgg | gcc | cgc | aac | ccc | tgc | aca | gat | ggc | cac | 6450 |
| Asp | Gly | Trp | Ser | Cys | Arg | Ala | Arg | Asn | Pro | Cys | Thr | Asp | Gly | His | |
| | | | 2130 | | | | | 2135 | | | | | 2140 | | |

| | | | | | | | | | | | | | | |
|---|---|---|---|---|---|---|---|---|---|---|---|---|---|---|
| cgc | ggg | ggc | tgc | agc | gag | cac | gcc | aac | tgc | ttg | agc | acc | ggc | ctg | 6495 |
| Arg | Gly | Gly | Cys | Ser | Glu | His | Ala | Asn | Cys | Leu | Ser | Thr | Gly | Leu | |
| | | 2145 | | | | | 2150 | | | | | 2155 | | | |

| | | | | | | | | | | | | | | |
|---|---|---|---|---|---|---|---|---|---|---|---|---|---|---|
| aac | aca | cgg | cgc | tgt | gag | tgc | cac | gca | ggc | tac | gta | ggc | gat | gga | 6540 |
| Asn | Thr | Arg | Arg | Cys | Glu | Cys | His | Ala | Gly | Tyr | Val | Gly | Asp | Gly | |
| | | | 2160 | | | | | 2165 | | | | | 2170 | | |

| | | | | | | | | | | | | | | |
|---|---|---|---|---|---|---|---|---|---|---|---|---|---|---|
| ctg | cag | tgt | ctg | gag | gag | tcg | gaa | cca | cct | gtg | gac | cgc | tgc | ttg | 6585 |
| Leu | Gln | Cys | Leu | Glu | Glu | Ser | Glu | Pro | Pro | Val | Asp | Arg | Cys | Leu | |
| | | 2175 | | | | | 2180 | | | | | 2185 | | | |

| | | | | | | | | | | | | | | |
|---|---|---|---|---|---|---|---|---|---|---|---|---|---|---|
| ggc | cag | cca | ccg | ccc | tgc | cac | tca | gat | gcc | atg | tgc | act | gac | ctg | 6630 |
| Gly | Gln | Pro | Pro | Pro | Cys | His | Ser | Asp | Ala | Met | Cys | Thr | Asp | Leu | |
| | | | 2190 | | | | | 2195 | | | | | 2200 | | |

| | | | | | | | | | | | | | | |
|---|---|---|---|---|---|---|---|---|---|---|---|---|---|---|
| cac | ttc | cag | gag | aaa | cgg | gct | ggc | gtt | ttc | cac | ctc | cag | gcc | acc | 6675 |
| His | Phe | Gln | Glu | Lys | Arg | Ala | Gly | Val | Phe | His | Leu | Gln | Ala | Thr | |
| | | 2205 | | | | | 2210 | | | | | 2215 | | | |

| | | | | | | | | | | | | | | |
|---|---|---|---|---|---|---|---|---|---|---|---|---|---|---|
| agc | ggc | cct | tat | ggt | ctg | aac | ttt | tcg | gag | gct | gag | gcg | gca | tgc | 6720 |
| Ser | Gly | Pro | Tyr | Gly | Leu | Asn | Phe | Ser | Glu | Ala | Glu | Ala | Ala | Cys | |
| | | | 2220 | | | | | 2225 | | | | | 2230 | | |

| | | | | | | | | | | | | | | |
|---|---|---|---|---|---|---|---|---|---|---|---|---|---|---|
| gaa | gca | cag | gga | gcc | gtc | ctt | gct | tca | ttc | cct | cag | ctc | tct | gct | 6765 |
| Glu | Ala | Gln | Gly | Ala | Val | Leu | Ala | Ser | Phe | Pro | Gln | Leu | Ser | Ala | |
| | | 2235 | | | | | 2240 | | | | | 2245 | | | |

```
gcc cag cag ctg ggc ttc cac ctg tgc ctc atg ggc tgg ctg gcc    6810
Ala Gln Gln Leu Gly Phe His Leu Cys Leu Met Gly Trp Leu Ala
            2250                2255                2260 aat ggc tcc act gcc cac cct gtg gtt ttc cct gtg gcg gac tgt    6855
Asn Gly Ser Thr Ala His Pro Val Val Phe Pro Val Ala Asp Cys
            2265                2270                2275 ggc aat ggt cgg gtg ggc gta gtc agc ctg ggt gcc cgc aag aac    6900
Gly Asn Gly Arg Val Gly Val Val Ser Leu Gly Ala Arg Lys Asn
            2280                2285                2290 ctc tca gaa cgc tgg gat gcc tac tgc ttc cgt gtg caa gat gtg    6945
Leu Ser Glu Arg Trp Asp Ala Tyr Cys Phe Arg Val Gln Asp Val
            2295                2300                2305 gcc tgc cga tgc cga aat ggc ttc gtg ggt gac ggg atc agc acg    6990
Ala Cys Arg Cys Arg Asn Gly Phe Val Gly Asp Gly Ile Ser Thr
            2310                2315                2320 tgc aat ggg aag ctg ctg gat gtg ctg gct gcc act gcc aac ttc    7035
Cys Asn Gly Lys Leu Leu Asp Val Leu Ala Ala Thr Ala Asn Phe
            2325                2330                2335 tcc acc ttc tat ggg atg cta ttg ggc tat gcc aat gcc acc cag    7080
Ser Thr Phe Tyr Gly Met Leu Leu Gly Tyr Ala Asn Ala Thr Gln
            2340                2345                2350 cgg ggt ctc gac ttc ctg gac ttc ctg gat gat gag ctc acg tat    7125
Arg Gly Leu Asp Phe Leu Asp Phe Leu Asp Asp Glu Leu Thr Tyr
            2355                2360                2365 aag aca ctc ttc gtc cct gtc aat gaa ggc ttt gtg gac aac atg    7170
Lys Thr Leu Phe Val Pro Val Asn Glu Gly Phe Val Asp Asn Met
            2370                2375                2380 acg ctg agt ggc cca gac ttg gag ctg cat gcc tcc aac gcc acc    7215
Thr Leu Ser Gly Pro Asp Leu Glu Leu His Ala Ser Asn Ala Thr
            2385                2390                2395 ctc cta agt gcc aac gcc agc cag ggg aag ttg ctt ccg gcc cac    7260
Leu Leu Ser Ala Asn Ala Ser Gln Gly Lys Leu Leu Pro Ala His
            2400                2405                2410 tca ggc ctc agc ctc atc atc agt gac gca ggc cct gac aac agt    7305
Ser Gly Leu Ser Leu Ile Ile Ser Asp Ala Gly Pro Asp Asn Ser
            2415                2420                2425 tcc tgg gcc cct gtg gcc cca ggg aca gtt gtg gtt agc cgt atc    7350
Ser Trp Ala Pro Val Ala Pro Gly Thr Val Val Val Ser Arg Ile
            2430                2435                2440 att gtg tgg gac atc atg gcc ttc aat ggc atc atc cat gct ctg    7395
Ile Val Trp Asp Ile Met Ala Phe Asn Gly Ile Ile His Ala Leu
            2445                2450                2455 gcc agc ccc ctc ctg gca ccc cca cag ccc cag gca gtg ctg gcg    7440
Ala Ser Pro Leu Leu Ala Pro Pro Gln Pro Gln Ala Val Leu Ala
            2460                2465                2470 cct gaa gcc cca cct gtg gcg gca ggc gtg ggg gct gtg ctt gcc    7485
Pro Glu Ala Pro Pro Val Ala Ala Gly Val Gly Ala Val Leu Ala
            2475                2480                2485 gct gga gca ctg ctt ggc ttg gtg gcc gga gct ctc tac ctc cgt    7530
Ala Gly Ala Leu Leu Gly Leu Val Ala Gly Ala Leu Tyr Leu Arg
            2490                2495                2500 gcc cga ggc aag ccc acg ggc ttt ggc ttc tct gcc ttc cag gcg    7575
Ala Arg Gly Lys Pro Thr Gly Phe Gly Phe Ser Ala Phe Gln Ala
            2505                2510                2515 gaa gat gat gct gac gac gac ttc tca ccg tgg caa gaa ggg acc    7620
Glu Asp Asp Ala Asp Asp Asp Phe Ser Pro Trp Gln Glu Gly Thr
            2520                2525                2530 aac ccc acc ctg gtc tct gtc ccc aac cct gtc ttt ggc agc gac    7665
Asn Pro Thr Leu Val Ser Val Pro Asn Pro Val Phe Gly Ser Asp
            2535                2540                2545
```

-continued

```
acc ttt tgt gaa ccc  ttc gat gac tca ctg  ctg gag gag gac ttc        7710
Thr Phe Cys Glu Pro  Phe Asp Asp Ser Leu  Leu Glu Glu Asp Phe
                2550                 2555                 2560 cct gac acc cag agg  atc ctc aca gtc aag  tgacgaggct ggggctgaaa      7760
Pro Asp Thr Gln Arg  Ile Leu Thr Val Lys
                2565                 2570 gcagaagcat gcacagggag gagaccactt ttattgcttg tctgggtgga tggggcagga    7820
ggggctgagg gcctgtccca gacaataaag tgccctcagc ggatgtgggc catgtcacc    7879
```